United States Patent [19]

Fuller et al.

[11] Patent Number: 5,792,668
[45] Date of Patent: Aug. 11, 1998

[54] RADIO FREQUENCY SPECTRAL ANALYSIS FOR IN-VITRO OR IN-VIVO ENVIRONMENTS

[75] Inventors: Milton E. Fuller, Reno, Nev.; David W. Deamer, Santa Cruz, Calif.; Mark N. Iverson, Reno; Ajit J. Koshy, deceased, late of Reno, both of Nev.

[73] Assignee: Solid State Farms, Inc., Reno, Nev.

[21] Appl. No.: 631,916

[22] Filed: Apr. 15, 1996

Related U.S. Application Data

[63] Continuation-in-part of Ser. No. 103,410, Aug. 6, 1993, Pat. No. 5,508,203.
[51] Int. Cl.$^6$ .................... G01N 27/00; G01N 33/50
[52] U.S. Cl. .................... 436/149; 73/53.01; 324/642; 422/82.01; 436/63; 436/79; 436/95; 436/108; 436/150; 436/151
[58] Field of Search .................... 128/633, 664, 128/665, 666, 635; 73/53.01; 324/642–646; 422/82.01; 436/63, 79, 95, 149, 150, 151, 108; 600/322, 347

[56] References Cited

U.S. PATENT DOCUMENTS

| | | | |
|---|---|---|---|
| 3,238,451 | 3/1966 | Shively | 324/646 |
| 4,407,290 | 10/1983 | Wilbur | 128/633 |
| 4,510,437 | 4/1985 | Iskander | 324/642 X |
| 4,679,426 | 7/1987 | Fuller et al. | 73/53.01 |
| 4,765,179 | 8/1988 | Fuller et al. | 73/53.01 |
| 4,812,738 | 3/1989 | Itaya et al. | 324/642 X |
| 4,880,014 | 11/1989 | Zarowitz et al. | 128/734 |
| 5,072,189 | 12/1991 | Openlander | 324/646 X |
| 5,077,476 | 12/1991 | Rosenthal | 250/341 |
| 5,103,181 | 4/1992 | Gaisford et al. | 324/642 X |
| 5,120,648 | 6/1992 | Lim et al. | 436/173.2 |
| 5,142,612 | 8/1992 | Shemik | 395/11 |
| 5,144,224 | 9/1992 | Larsen | 324/631 X |
| 5,233,306 | 8/1993 | Misra | 324/642 X |
| 5,508,203 | 4/1996 | Fuller et al. | 436/149 |

OTHER PUBLICATIONS

V.K. Benzar et al, *Chem. Abstr.* 1974, 80, 17133V.
A Suggett et al, *J. Solution Chem.* 1976, 5, 1–15.
E. Tanabe et al, *IEEE Trans. Instrum. Meas.* 1976, IM25, 222–226.
G. Delbos et al, *J. Microwave Power* 1978, 13, 69–76.
V.V. Tyazhelov et al, *Chem. Abstr.* 1979, 91, 135969X.
E.C. Burdette et al, *IEEE Trans. Microwave Theory Tech.* 1980, 28, 414–427.

(List continued on next page.)

*Primary Examiner*—Arlen Soderquist
*Attorney, Agent, or Firm*—Flehr Hohbach Test Albritton & Herbert LLP

[57] ABSTRACT

Concentration of a target chemical in the presence of other substances in a specimen is determined by subjecting the specimen to radio frequency electromagnetic components, sequentially or otherwise, ranging to about 5 GHz. The reflected and/or transmitted signal real and imaginary components at the specimen are spectrally examined as a function of frequency to identify the presence and/or concentration of the chemical of interest. Such examination includes analysis of the effective complex impedance presented by the specimen, and/or effective phase shift between the transmitted and reflected signal at the specimen. The effects upon glucose concentration measurements of varying electrolytes, primarily NaCl, can be nulled-out by examining impedance magnitude at a cross-over frequency, for example about 2.5 GHz. NaCl concentration exhibits a very linear relationship with phase shift change at frequencies in the 2 GHz–3 GHz range. In a specimen that is blood, such phase shift measurements provide data proportional to NaCl concentration. Impedance magnitude measurements using 1 MHz to 400 MHz frequencies provides a measure of combined concentration of glucose and NaCl. The phase shift data may then be used to substrate out the NaCl concentration from the combined concentration, to yield a good measure of glucose concentration. Such tests may be conducted in-vitro or in-vivo and lend themselves to blood level glucose analyses by diabetics.

17 Claims, 14 Drawing Sheets

OTHER PUBLICATIONS

M.A. Stuchly et al, *Bioelectromagnetics* 1981, 2, 93–103.

M.A. Stuchly et al, *Int. J. Electron.* 1984, 56, 443–456.

S. Ray et al, *J. Bioelectro* 1987, 6, 71–92.

A. Surowiec et al. *Phys. Med. Biol.* 1987, 32, 615–621.

R. Pottel et al. *Biomed. Technik* 1990, 35, 158–161.

C. L. Davey et al. *Eur. Biophys. J.* 1990, 18, 255–266.

G.G. Kramer et al. *Neurological Res.* 1992, 14, 255–258.

W.M. Arnold et al, *Biochim. Biophys. Acta* 1993, 1157, 32–44.

T. Skodvin et al. *J. Colloid Interface Sci.* 1993, 155, 392–401.

P.M.J.M. deVries et al, *Med. Biol. Eng. Comput.* 1993, 31, 445–448.

C. Gabriel *Repwt* AF OSR–TR–93–0706, 1993.

H.P. Schwan *Med. Prog. Tech.* 1993/94, 19, 163–165.

T. Skoduin et al. *J. Colloid Interface Sci* 1994, 166, 43–50.

H. Beving et al, Eur. J. Surgery 1994, S574, 87–89.

S. Nelson et al, *J. Microwave Power Electromag. Energy* 1994, 29, 81–93.

A.M. Woodward et al, *Bioelectrochem. Bioenerg.* 1996, 40, 99–132.

Zumdahl, *Chemistry*, 1986, p. 238.

Serway, Physics, for Scientists and Engineers/with Modern Physics, 1983, pp. 756–757.

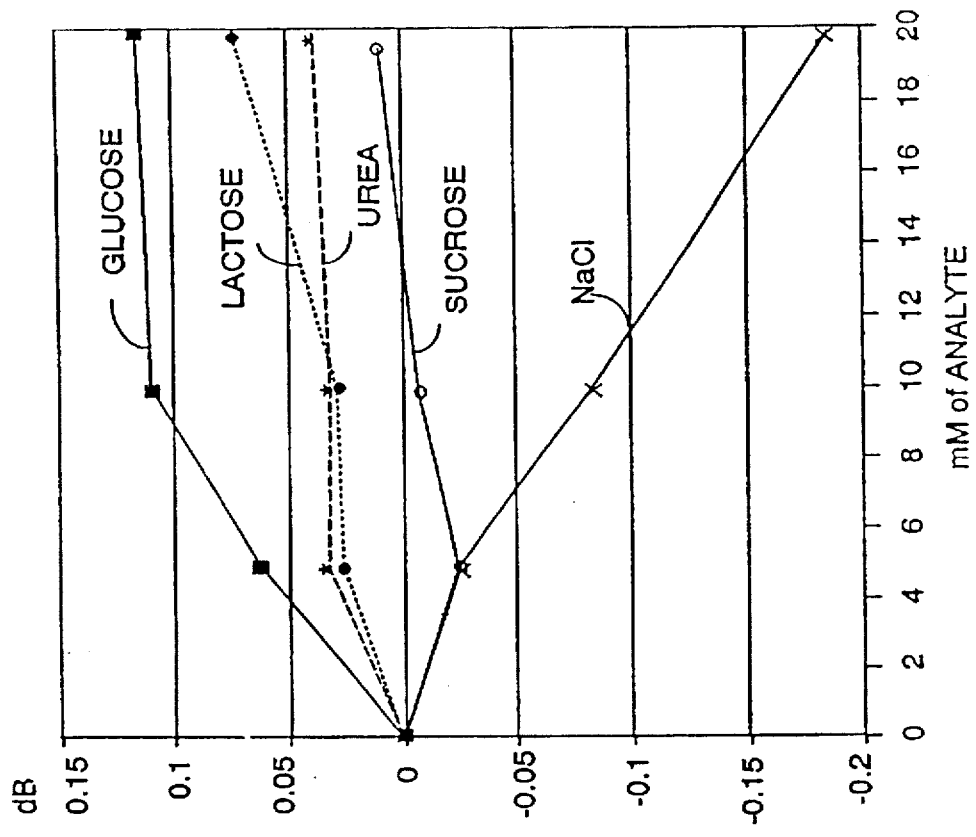
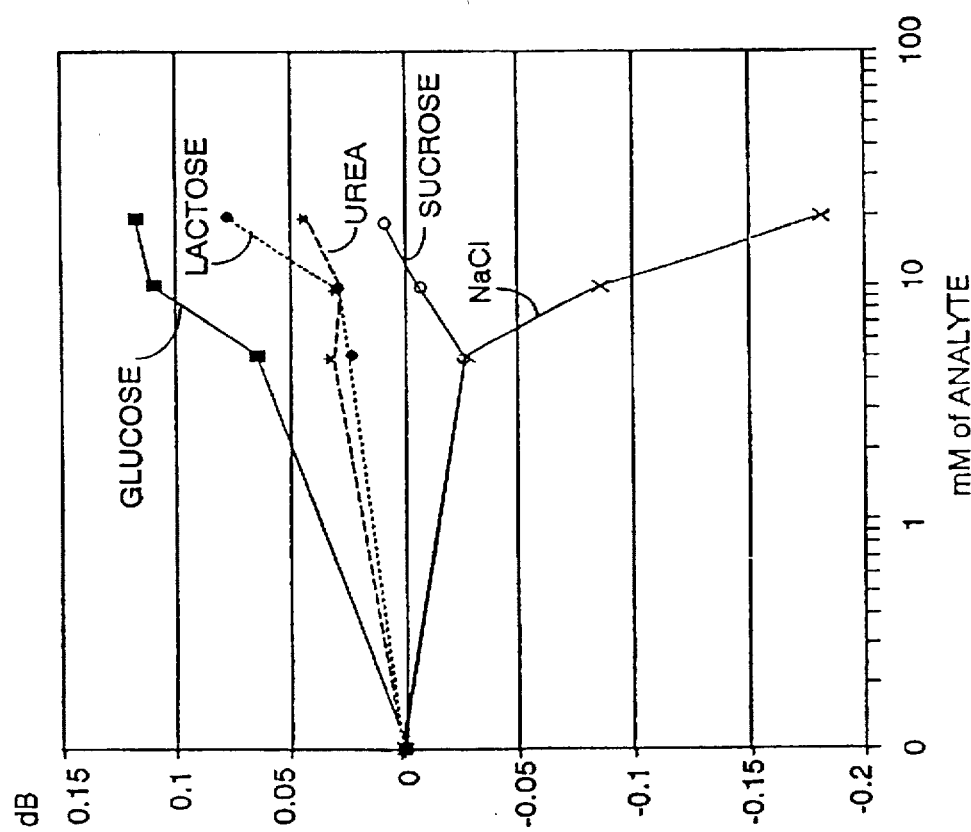

5,792,668

RADIO FREQUENCY SPECTRAL ANALYSIS FOR IN-VITRO OR IN-VIVO ENVIRONMENTS

RELATIONSHIP TO PREVIOUSLY FILED PATENT APPLICATION

This is a continuation-in-part of patent application Ser. No. 08/103,410, filed 6 Aug. 1993 entitled APPARATUS AND METHOD FOR RADIO FREQUENCY SPECTROSCOPY USING SPECTRAL ANALYSIS, now U.S. Pat. No. 5,508,203.

FIELD OF THE INVENTION

This invention relates generally to radio frequency spectroscopy, and more particularly to improving specificity and accuracy of such analysis to determine the presence and/or concentration of a desired chemical among other substances within a specimen.

BACKGROUND OF THE INVENTION

Many conventional analysis techniques measure the concentration of a chemical in a test specimen or sample, even where the specimen contains a complex mixture of chemicals. Such techniques include mass spectrophotometry, nuclear resonance, flame photometry, conductance and refractometry. While these techniques work, unfortunately, their accuracy is too often directly related to their cost. Further, many such techniques alter or destroy the specimen under test, and require relatively elaborate equipment.

More recently attempts have been made to determine various properties of materials, using sound, electromagnetic waves, or single pulses as the basis for analysis. In contrast to conventional chemical analysis, wave and pulse-based techniques can provide a non-invasive in-vivo analysis.

For example, U.S. Pat. No. 4,679,426 (July 1987) discloses a non-invasive in-vivo technique for measuring concentration of chemicals, sodium chloride for example. Periodic electromagnetic waves having a repetition rate of about 10 MHz to 100 MHz were coupled to a subject's finger, and sodium or chloride ions within the finger apparently distorted these waves. This distortion in the composite waveform was received from the finger, using the same electrode-antenna pair used to couple the waves to the finger. The composite waveform distortion was then examined, and found to provide meaningful data as to chemical concentrations.

Glucose is an especially important chemical, a knowledge of whose absolute concentration level can be vital to diabetics. Several techniques for providing blood-sugar analysis are known, which permit subjects to determine their own glucose levels. Unfortunately many such techniques require invasive sampling of the subject.

One non-invasive technique for determining glucose levels in-vivo was disclosed in U.S. Pat. No. 4,765,179 (August 1988) in which a periodic train of electromagnetic energy, preferably having a repetition rate of about 1 MHz to 1 GHz, was coupled to a subject's finger. The composite waveform distortion was then analyzed and found to provide meaningful analysis of glucose levels in the range of about 50 to 150 mg percent. However, beyond about 110 mg percent, it was desirable to fine-tune the electromagnetic energy to maintain measurement accuracy.

Understandably, blood is a complex solution. Monitoring the concentration of glucose in blood presents substantial challenges to discriminate against other substances in the blood that may mask or alter the analysis results.

U.S. Pat. No. 5,508,203 described a non-invasive in-vivo apparatus and method for determining a chemical level in a subject, including the chemical glucose. The use of frequencies up to about 1 GHz was disclosed and the disclosed apparatus permitted even lay persons including diabetics to determine, for example, the level of glucose in their blood system.

As useful as the invention disclosed in U.S. Pat. No. 5,508,203 is, applicants have since realized that electrolytes, e.g., NaCl, KCl, $Na_2HPO_4$, and $KH_2PO_4$ of varying concentrations in human blood can affect the accuracy of glucose measurements using that invention. In the human system, glucose concentrations typically range 60 mg/dl to about 150 mg/dl for a non-diabetic, and range from about 50 mg/dl to 500 mg/dl. In the human population, NaCl concentrations can range from about 135 mM to about 145 mM. To effectively and confidently measure glucose and/or its concentration in blood, a resolution of about 10 mg/dl of glucose is desired. Non-invasive sophisticated laboratory grade test equipment can resolve glucose in-vitro to perhaps 1.5 mg/dl. Invasive consumer-grade can resolve glucose to perhaps 5 mg/dl with an accuracy of perhaps ±10%. Applicants are not aware of existing non-invasive devices for resolving glucose to the desired 10 mg/dl level.

There is a need for a method and apparatus to reduce the varying concentration effects of electrolytes, especially NaCl, when measuring glucose concentrations in human blood. Such method and apparatus should be useable in-vitro and in-vivo, and should work in non-invasive in-vivo measurement environments. Further, such method and apparatus should be capable of use by lay persons. Such method and apparatus should also have applicability in measurements unrelated to analysis of bodily fluid, including applications in industry.

The present invention discloses such a method and apparatus.

SUMMARY OF THE INVENTION

A specimen containing a chemical of interest as well as other substances is via probes subjected to radio frequency electromagnetic signals having high frequency components extending to perhaps 5 GHz. Preferably such frequencies are sequentially presented using one sinewave frequency at a time, although simultaneously presented multiple frequencies may also be useful. Reflected and/or transmitted signal real and imaginary components at the specimen are then spectrally examined as a function of frequency to identify the presence and/or concentration of the chemical of interest. Such examination includes analysis of the effective complex impedance presented by the specimen, and/or effective phase shift between the transmitted and reflected signal at the specimen. In this manner, greater specificity can be attained with respect to detecting presence and/or concentration of a desired analyte or chemical of interest.

For in-vitro measurements, a probe is inserted into the specimen and is coupled to a network analyzer, or similar electronic system. In such in-vitro measurements, the specimen may include blood or other bodily fluid, or may be a substance unrelated to bodily fluid. In in-vivo measurements, a network analyzer of similar electronic system may be coupled to electrode(s) on a probe. The probe is pressed against a subject's body, preferably a finger, and non-invasive analyses are made.

Applicants have discovered that variable concentrations of electrolytes, especially NaCl, affect accuracy and specificity of glucose concentration measurements. At frequencies below about 1 GHz, increasing NaCl (or other small ions) concentration decreases impedance, whereas at higher frequencies the impedance is increased. Applicants believe that at the lower frequencies, ions can respond to the changing electromagnetic field adjacent to the probe ends, whereas this is more difficult at higher frequencies, whereat water dipoles appear to largely determine impedance. In general, applicants have learned that over a wide frequency regime, higher glucose concentrations increases impedance, probably because the large glucose molecules hamper movement of electrolyte ions and water dipoles in a solution specimen. Of special interest, applicants have discovered that increasing NaCl concentrations over a wide frequency regime increase phase shift in a linear fashion, which phase shift is insensitive to glucose concentrations. Using these discoveries, applicants can null-out or at least reduce or compensate for electrolyte concentration effects upon glucose concentration by using cross-over frequencies, and by examining different measurement parameters at different frequency regimes.

In a blood specimen, electrolyte concentration effects are effectively "tuned out" by examining the magnitude of complex impedance using a cross-over frequency of approximately 2.5 GHz. This use of a cross-over frequency and complex impedance measurement provides low sensitivity to NaCl concentration and thus more accurate and specific glucose concentration readings. Such analysis improvement can be highly important, for example when the specimen comes from a diabetic or suspected diabetic.

Differential analyses may be made by combining impedance magnitude and phase shift measurement data. For example, high frequency phase shift measurements taken between 2 GHz and perhaps 5 GHZ can provide data proportional to magnitude of ion concentration, particularly NaCl. On the other hand, impedance magnitude measurements made using lower frequencies, perhaps the 1 MHz to 400 MHz range, will provide a measure of combined concentration of glucose and ion concentration, again primarily NaCl. The high frequency phase shift data may be used to subtract out the effective NaCl concentration from the lower frequency impedance total concentration data. The result is a lower frequency measure of glucose concentration in the specimen, a frequency regime in which measurement equipment is quite sensitive.

Analysis equipment coupled to the impedance measurement data and phase shift measurement data can include look-up tables or the like, correlating phase shift data to NaCl concentration levels. For industrial applications, the look-up tables can store data correlating impedance, phase shift and frequency measurements to known substances and concentration levels. This information can then be used to enhance nulling-out of NaCl in an impedance measurement made at a cross-over frequency.

Output indicators coupled to such analysis equipment can enable even a lay user to readily understand what chemical has been detected and at what concentration, or simply to confirm that a safe concentration has been detected for the chemical of interest.

Other features and advantages of the invention will appear from the following description in which the preferred embodiments have been set forth in detail, in conjunction with the accompanying drawings.

BRIEF DESCRIPTION OF THE DRAWINGS

FIGS. 4A, 4B, and 4C depict signal amplitudes provided by the system of FIG. 1 for different target chemicals in analyte test solutions;

DETAILED DESCRIPTION OF THE PREFERRED EMBODIMENT

Figure 1:
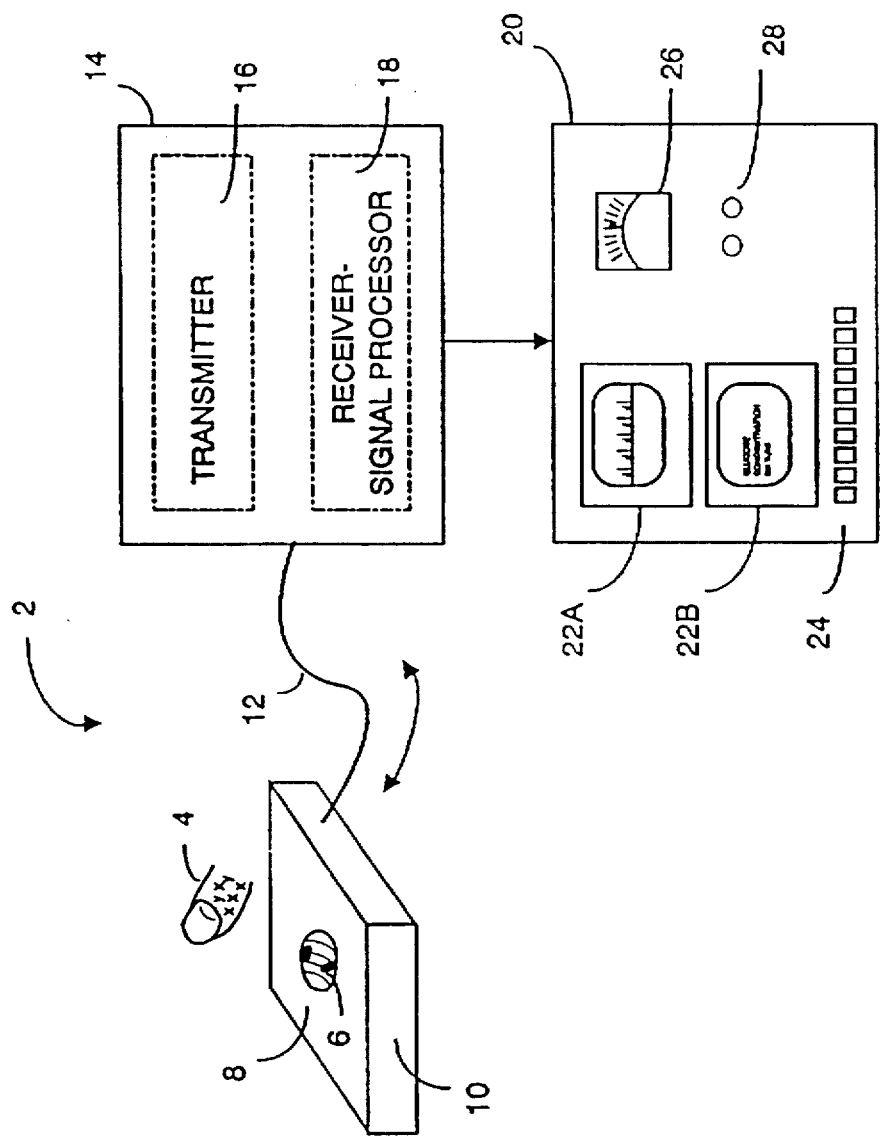
FIG. 1 is a block diagram of a radio frequency spectroscopy system.

FIG. 1 depicts a radio frequency ("RF") spectroscopy system 2 for determining the presence of one or more target chemicals (depicted as x, y) in a cell membrane specimen 4, e.g., a human finger. The specimen finger 4 is pressed against a probe pair 6, preferably disposed within a concave depression 8 formed in a lucite base 10. Probe pair 6 comprise two conductive rods that protrude slightly from the depression 8, permitting electrical contact to be made when finger 4 is pressed against the rods. Preferably the rods are brass, perhaps 0.2" (5 mm) outer diameter and protrude outward from the concave surface about 0.05" (1.3 mm), and into the lucite base about 0.5" (12 mm). Of course other tissue could be probed, e.g., an ear, and the specimen need not be a human.

A pair of transmission lines 12 electrically couples the electrode pair to a system 14 that includes a transmitter unit 16 and receiver-signal processor unit 18. Briefly, unit 16 transmits a high frequency signal via transmission lines 12 to probes 6, which couple the signal to the specimen finger 4. Although the precise mechanism is not fully understood, it appears that the presence of target chemicals, e.g., x and/or y, within the specimen may cause energy transfer of certain spectra of the source signal from transmitter 16. The result is that a return signal from the specimen, present at probe pair 6 and coupled via transmission lines 12 to unit 18, differs from the source signal. Of course separate probe units 6 could be used to couple the transmitter unit 16 to the specimen, and to couple the return signal from the specimen to unit 18.

Unit 18 receives and processes the return signal such that spectral signatures associated with the presence and concentration of various target chemicals within the specimen can be recognized. The processed data is then coupled to a display system 20 that conveys the detected information to a user. Operation of the receiver-signal processor unit 18 can be tailored, manually or automatically by a neural network, to recognize specific target chemicals, for example glucose within the blood stream within finger specimen 4. In such instance, the various output devices within display system 20 might provide a user with calibrated data as to his or her glucose concentration.

Display system 20 may include a monitor that can display a spectrum analyzer output (22A), and/or alpha-numeric/ graphical output (22B). Display system 20 may also include a bar graph or alpha-numeric indicator 24 indicating, for example, the concentration level of the target chemical, for example, glucose. A calibrated output meter 26 could provide the user with concentration data. Alternatively, a simple "GO/NO GO" output indicator 28 could alert the user that excess glucose concentration has been detected. A diabetic user would thus be alerted to take insulin immediately.

Figure 2:
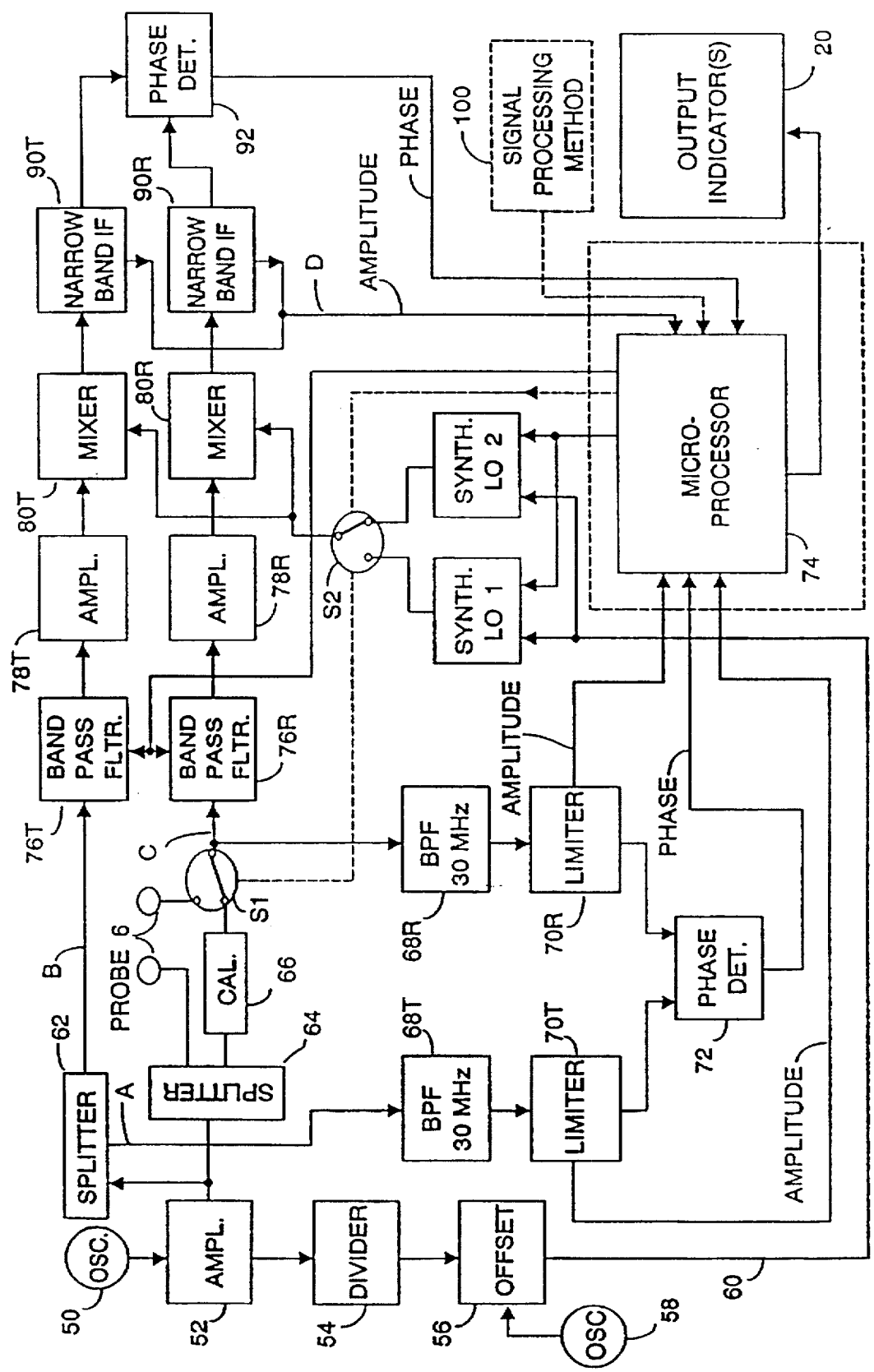
FIG. 2 is a block diagram of the transmitter/receiver-signal processing system 14, shown in FIG. 1.

FIG. 2 is a block diagram of the transmitter/receiver-signal processing system 14. Oscillator 50 generates a high frequency stimulus signal that will be transmitted via probes 6 to specimen 4. In the preferred embodiment, oscillator 50 provides a 30 MHz fundamental square wave having a 50% duty cycle, and transition times of a few nanoseconds. As such, the oscillator output frequency spectrum will be rich in harmonics, the odd-numbered harmonics predominating. In the frequency domain, a perfect square-wave source signal would have harmonics with a sin(x)/x envelope, where x represents a harmonic frequency.

The spectral output of such an oscillator 50 is commonly referred to as a comb spectra, as the various spectra are uniformly spaced similar to the teeth on a comb. The power output level at the oscillator output is preferably about 1 mW, which is 0 dBm, although other power levels may also be used.

In the preferred embodiment, the various source signal spectra are harmonically related since generation of a pulse train provides the harmonic frequencies automatically. However the source frequencies need not be harmonically related, and a single oscillator 50 may be rapidly changed between discrete frequencies (e.g., in the manner of spread spectrum transmitters). Alternatively, oscillator 50 could comprise a plurality of signal generators whose separate frequency outputs may or may not be harmonically related. If harmonically related, one such generator could provide a sinusoidal output at a fundamental frequency, e.g., 30 MHz. A second generator could provide a 60 MHz sinusoidal output, a third generator could provide a 90 MHz sinusoidal output, and so forth. In a different embodiment, one such generator might provide an output at frequency f1, a second generator might provide an output at f2, not harmonically related to f1, and so forth.

As used herein, oscillator 50 is understood to be a source of electromagnetic signal that contains a plurality of high frequency components, regardless of whether such components represent harmonics of a single source frequency, or represent many source frequencies, that need not be harmonically spaced-apart.

Unit 52 preferably includes an amplifier stage and a power splitter, and comprises a MAR-3 amplifier and a Cougar amplifier stage and a power splitter in the preferred embodiment. These commercially available components boost the oscillator signal provided to divider 54 to about 15 dBm, and provided to power splitters 62, 64 to about 3 dBm. In turn, each power splitter 62, 64 divides the thus amplified signal into two signals at nodes A and B, each having 0 dBm power output. Splitters 62, 64 are preferably wideband, e.g., about 10 MHz to 1,000 MHz (or 1 GHz).

The intermediate frequency ("IF") for system 14 is preferably 21.4 MHz, an intermediate frequency commonly used in commercial equipment, for which frequency many standardized transformers and circuits are readily available. High-side mixing injection preferably is used. Thus, to generate a local oscillator frequency that is 21.4 MHz higher than a center frequency, it is necessary to develop a synthesized reference 6.4 MHz signal. Unit 54 divides the fundamental frequency of the oscillator signal by 6, to yield a nominal 5.0 MHz reference signal.

This 5.0 MHz reference signal and a 6.4 MHz phase-locked crystal controlled oscillator signal 58 are processed by offset module 56. Offset module 56 outputs on line 60 a signal having a frequency of 6.4 MHz that is phase locked to the 30 MHz frequency of oscillator 50. Because phase lock loop systems are well known in the art of digital signal processing design, further details of the generation of the frequency locked 6.4 MHz signal on line 60 are not presented here.

In FIG. 2, calibrator unit 66 is an electronic model of a typical human finger, essentially the electronic equivalent circuit of a finger specimen 4. While calibration unit 66 approximates the specimen impedance, unit 66 will not include the target chemical.

Figure 3B:
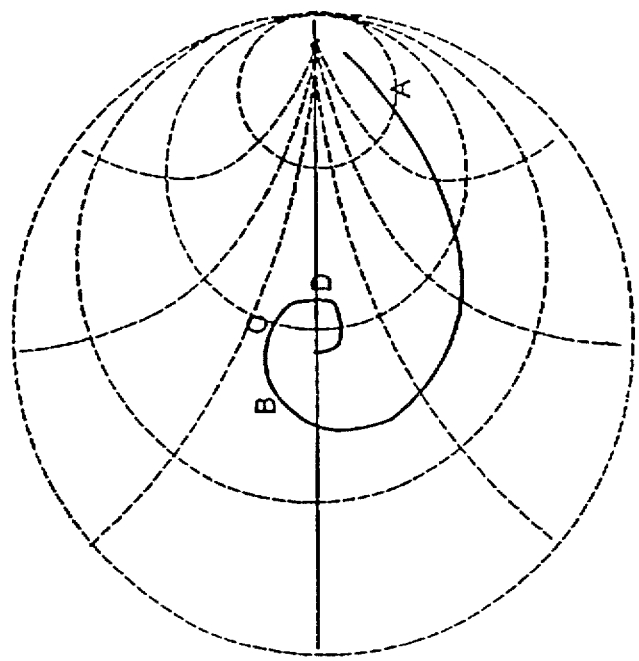
FIG. 3B is a Smith chart impedance versus frequency representation of the equivalent circuit depicted in FIG. 3A.
Figure 3A:
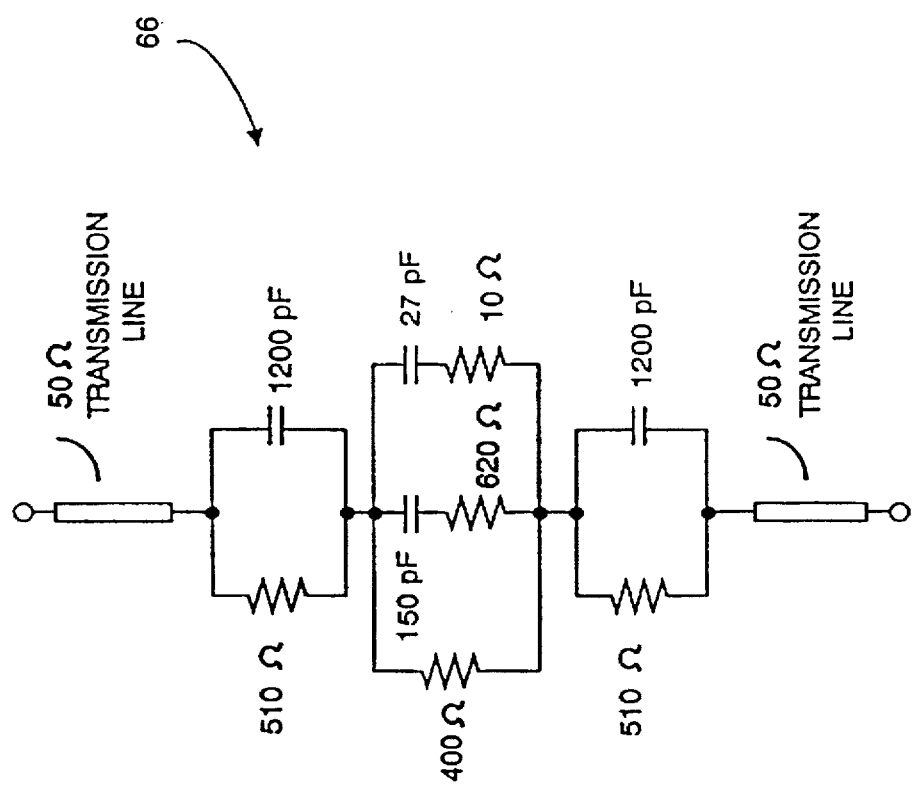
FIG. 3A is a schematic of the calibration cell 66, depicted in FIG. 2.

FIG. 3A details the circuitry within calibration unit 66, namely two segments of transmission line having 50 Ω impedance at 400 MHz, and assorted resistors and capacitors. The transmission lines, resistors and capacitors were selected empirically by comparing frequency versus impedance data from human fingers with data from the equivalent circuit of FIG. 3A. FIG. 3B is a Smith chart impedance versus frequency representation of the equivalent circuit of FIG. 3A. Point A in FIG. 3B represents an impedance of about 192 Ω/−201 Ω at 10 MHz, point B is 39.5 Ω/11.5 Ω at 300 MHz, C is 52 Ω at 400 MHz, and point D is about 57 Ω/−2.6 Ω at 500 MHz.

With further reference to FIG. 2, as will now be described, various components are replicated to provide a processing path for the transmitted source signal, and to provide a processing path for what will be termed the sampled return (or received) signal. The sampled return signal advantageously permits compensating the system of FIG. 2 for component variations and drift between what will be termed the received and the transmitted signal processing paths.

More specifically, the response of specimen 4 to the source signal (e.g., the return signal at the probe pair 6) is switchably sampled by switch S1 with the response of the calibration unit 66 to the source signal. Harmonic frequency-by-frequency, the output from probe pair 6 and from calibration unit 66 are sampled, the output of S1 providing a sampled return signal at node C to the remainder of system 18. Of course, if source oscillator 50 provided discrete frequencies that were not harmonically related, it is understood that frequency-by-frequency, the output from probe pair 6 and from calibration unit 66 would be sampled. In the preferred embodiment, the frequency bands of interest begin with about the sixth or seventh harmonic of source oscillator 50, e.g., about 195 MHz, and extend to about 1 GHz, or higher, which range is the bandwidth of system 18. Within that bandwidth, individual frequencies are sampled between probe pair 6 and calibration unit 66.

Switch S1 preferably is a commercially available monolithic microwave integrated circuit ("MMIC"), a relay, or other switching mechanism. S1 switches between the probe 6 output and the calibrator under control of a microprocessor 74 within system 14. In the preferred embodiment, microprocessor 74 was a Motorola 68HC11, although other microprocessors could be used instead.

S1 may sample the output of probe 6 for a time period ranging from perhaps 90 ms to perhaps 7 seconds, and then may sample the output of the calibration unit 66 for a time period also within that range, the duty cycle typically being aperiodic. For example, during the time S1 is coupled to probe 6, the probe output signal is sampled for one or more frequencies that are harmonics of the fundamental frequency of oscillator 50 (or for one or more discrete frequencies provided by an oscillator 50 that does not provide harmonics). During the time S1 is coupled to the calibration unit 66, the response of calibration unit 66 to one or more frequencies that are harmonics of the fundamental oscillator 50 frequency are sampled.

Understandably, if components 76T and 76R, 78T and 78R, 80T, 80R, 90T and 90R (to be described) were identical and exhibited no drift, calibration unit 66 could be dispensed with, and S1 replaced by a wire making a permanent connection in the probe 6 S1 position. Such an ideal system would require no mechanism for compensating for drift and other differences in the signal processing paths for the harmonics of the oscillator signal 50, and for the harmonics in the return signal obtained from probe 6.

In practice, variations in temperature and/or pressure between probe pair 6 and the tissue in the specimen 4 may contribute some error to the measurement process. To permit microprocessor 74 to compensate for such error, in addition to providing the microprocessor with phase and amplitude information for harmonics, phase and amplitude information is also provided for the oscillator fundamental frequency. This frequency has been found experimentally to be sensitive to such temperature and/or pressure variations. It is understood that suitable temperature and/or pressure transducers and analog-to-digital conversion components that are not shown in FIG. 1 are used.

As shown in FIG. 2, within the transmitted source signal processing path, a bandpass filter 68T has a center frequency equal to that of oscillator 50, e.g., 30 MHz, and a bandwidth of about 1 KHz to perhaps 1 MHz. Other bandwidths could be used and in fact, a 30 MHz lowpass filter might instead be used. The transmitted signal from node A is coupled to bandpass filter 68T, and the 30 MHz center frequency component of this signal passes from filter 68T and is amplitude limited by limiter 70T. The thus bandpass filtered and amplitude limited signal is coupled to an input of a phase detector 72.

In a parallel path, the sampled return signal from switch S1, present at node C, passes through a similar 30 MHz bandpass filter 68R, amplitude limiter 70R to provide a second input to phase detector 72. (The letter T or R attached to a reference element herein denotes that the element is used in the transmitted source path, e.g., 68T, or is used in the sampled return signal path, e.g., 68R.)

Phase detector 72 compares the difference in phase between the transmitted 30 MHz fundamental frequency and the sampled return 30 MHz fundamental frequency signal. The phase detector 72 output signal voltage will be proportional to such phase shift, e.g., a number of mV per each degree of phase shift. As shown in FIG. 2, the phase output information from detector 72 is coupled to microprocessor 74 for analysis.

Proceeding horizontally across the top of FIG. 2, parallel paths are also depicted for processing the transmitted source signal harmonics (available at node B) and the sampled return signal harmonics from switch S1 (available at node C). These two horizontal paths use substantially identical components (as denoted by the nomenclature) to provide transmitted and sampled return signals at an intermediate frequency (IF) that is about 21.4 MHz in the preferred embodiment.

Briefly, the components now to be described resolve the harmonic frequency components of the signals at node B and node C into preferably four bands of discrete frequencies, depending upon what harmonics of the source oscillator signals are desired to be examined.

Much of the remainder of the signal processor functions as a scanner-receiver, that under microprocessor control scans discrete harmonic frequencies of interest. The transmitted source signal path components will first be described, it being understood that identical components are used in the parallel sampled return signal path, as indicated by the nomenclature, e.g., 76T, 76R, 78T, 78R, etc. Bandpass filter 76T (and thus also 76R) preferably is a filter bank that includes an internal MMIC switching mechanism operating under control of microprocessor 74. The input port of filter 76T passes the transmitted signal from node B through an internal switch into two banks of pre-shaping three-pole bandpass filters. These first two internal filter banks have bandpasses of 195 MHz to 395 MHz, and 395 MHz to 805 MHz. Still within filter bank 76T, the outputs from the 195–395 MHz and 395–805 MHz filters pass through additional internal MMIC switches and bandpass filters. These additional filters pass 195–295 MHz, 295–405 MHz, 405–610 MHz, and 605–815 MHz. Still within 76T, the variously filtered components are combined into a single signal that is amplified by amplifier 78T.

In similar fashion, the sampled return signal at node C is passed through switching bandpass filters within bandpass filter bank 76R, and the variously filtered components are combined and amplified by amplifier 78R. While the operation of bandpass filter banks 76T, 76R has been described with reference to specific frequency bands, those skilled in the art will recognize that the frequencies comprising the signals at nodes B and C may be filtered using bandpass filters having different ranges of bandpass. Because the design of units 76T, 76R is known to those skilled in the relevant art, schematics are not here provided.

For example, if the target chemical of interest is best resolved by examining say the seventh harmonic of the 30 MHz transmitted source signal (or a given discrete frequency of a source signal providing a plurality of frequencies not necessarily harmonically related), microprocessor 74 is caused to control the switching within units 76T, 76R to pass 210 MHz frequency components, e.g., to select the 195 MHz–295 MHz bandpass. Amplifiers 78T, 78R preferably have sufficient gain to compensate for attenuation caused by filters 76T, 76R, and have a bandwidth of at least 195 MHz to 815 MHz.

Of course, if amplifiers 78T, 78R were ideal and not subject to front-end overload, it would be possible to delete the bandpass filter systems 76T, 76R, and rely upon the operation of mixers 80T, 80R, and narrow band IF units 90T, 90R (to be described), to separate the various harmonic components of the oscillator signal and of the return signal.

As shown by FIG. 2, the output signals from amplifiers 78T, 78R are provided as an input signal to mixers 80T, 80R. Frequency synthesized local oscillators LO1 or LO2 provide respective second input signals to mixers 80T, 80R, via a MMIC switch S2 (or similar device) that switches between the two synthesized oscillator signals under control of microprocessor 74.

The synthesized LO1 or LO2 signals are then frequency mixed against the selective spectral components of the transmitted source signal and sampled return signal that have been switchably selected to pass through filter banks 76T, 76R. The LO1 or LO2 output signals are 21.4 MHz above the harmonic frequency of interest. Because of the difficulty associated with implementing a synthesized local oscillator whose output frequency can range from about 231.4 MHZ (e.g., 7×30 MHz+21.4 MHz) to perhaps 800 Mhz (e.g., about the twenty-sixth harmonic 26×30 MHz+ 21.4 MHz), the preferred embodiment employed two local oscillators, LO1, LO2. If, however a suitable synthesized oscillator having a two-octave frequency output could be implemented, such oscillator would replace LO1, LO2 and the necessity for S2.

Stages 90T, 90R are narrowband intermediate frequency circuits that pass a 21.4 MHz center frequency with a bandwidth of about 25 KHz. Of course by suitably offsetting mixing frequencies, an IF of other than 21.4 MHz could be used. In the preferred embodiment, IF units 90T, 90R are similar to IF units commonly found in commercially available cellular telephones.

The harmonic frequency information passing through IF units 90T and 90R are input to phase detector 92. Phase detector 92 compares transmitted source and sampled return signals at each harmonic frequency of interest. The difference in phase between these signals is then provided by phase detector 92 to microprocessor 74. At the same time, the relative voltage levels from the IF units 90T, 90R at node D are also provided (after suitable analog to digital conversion, converter not shown) to microprocessor 74.

To recapitulate, microprocessor 74 receives phase information from detector 92 that is relative to the various harmonics of the source signal (or discrete frequencies of interest if a non-harmonic generator 50 is employed), and that is relative to the various harmonics (or discrete frequencies) of the source signal as altered by the target substance and received at the probe pair 6. Similarly, microprocessor 74 receives amplitude information of IF units 90T and 90R relative to the various harmonics (or discrete frequencies of interest) of the source signal, and that is relative to the various harmonics (or discrete frequencies) of the source signal as altered by the target substance and received at probe pair 6. Further, to permit compensation for probe temperature and/or probe-specimen pressure variations, limiters 70T, 70R provide microprocessor 74 with amplitude of the source frequency, and with amplitude of the source frequency as altered by the target substance and received at probe pair 6, while detector 72 provides similar phase information for the source frequency.

Microprocessor 74 operates under program control, generating data for further processing by a so-called neural network, look-up table, algorithm, or other method of signal processing, shown symbolically in FIG. 2 as element 100. In a manner known to those skilled in the relevant art, a neural network 100 can be "trained" to recognize a spectral signature associated with a given target chemical, glucose for example. To ease this recognition, neural network 100 can optimize the manner of signal processing within unit 14.

For example, the operation of filter banks 76T, 76R can be altered under control of microprocessor 74. In a more generalized embodiment, the number and bandwidth of individual bandpass filters within units 76T, 76R could be dynamically modified by suitable MMIC-selection, all under microprocessor control. However, unit 100 may simply be a look-up table, correlating relative amplitude changes in a return signal with harmonic frequency against presence or concentration of a target chemical in the specimen. Further, a suitable neural network 100 might control microprocessor 74 to optimize the generation of discrete frequencies, based upon processed signature data. For example, if a certain set of frequencies from oscillator 50 provided a slight spectral signature, network 100 might direct oscillator 50 to provide slightly different frequencies until the signature was more recognizable.

Microprocessor 74 in turn provides output signals to output indicator(s) 20. As has been described, output indicator(s) 20 can, in a variety of formats, display information enabling a user to determine the presence and concentration of a desired target chemical (e.g., x) in a specimen. In the preferred embodiment, the specimen is in fact a finger of the individual using the disclosed system. Although the system shown in FIGS. 1 and 2 was implemented in breadboard fashion, those skilled in the art will appreciate that it may in fact be fabricated in a handheld, battery operated, portable unit. In such embodiment, output indicator(s) 20 would preferably include liquid crystal displays (LCDs) or simple GO/NO GO indicators, to preserve power and space. Preferably base 10 would be attached to the case housing the remainder of the system for ease of portability.

Figure 4C:
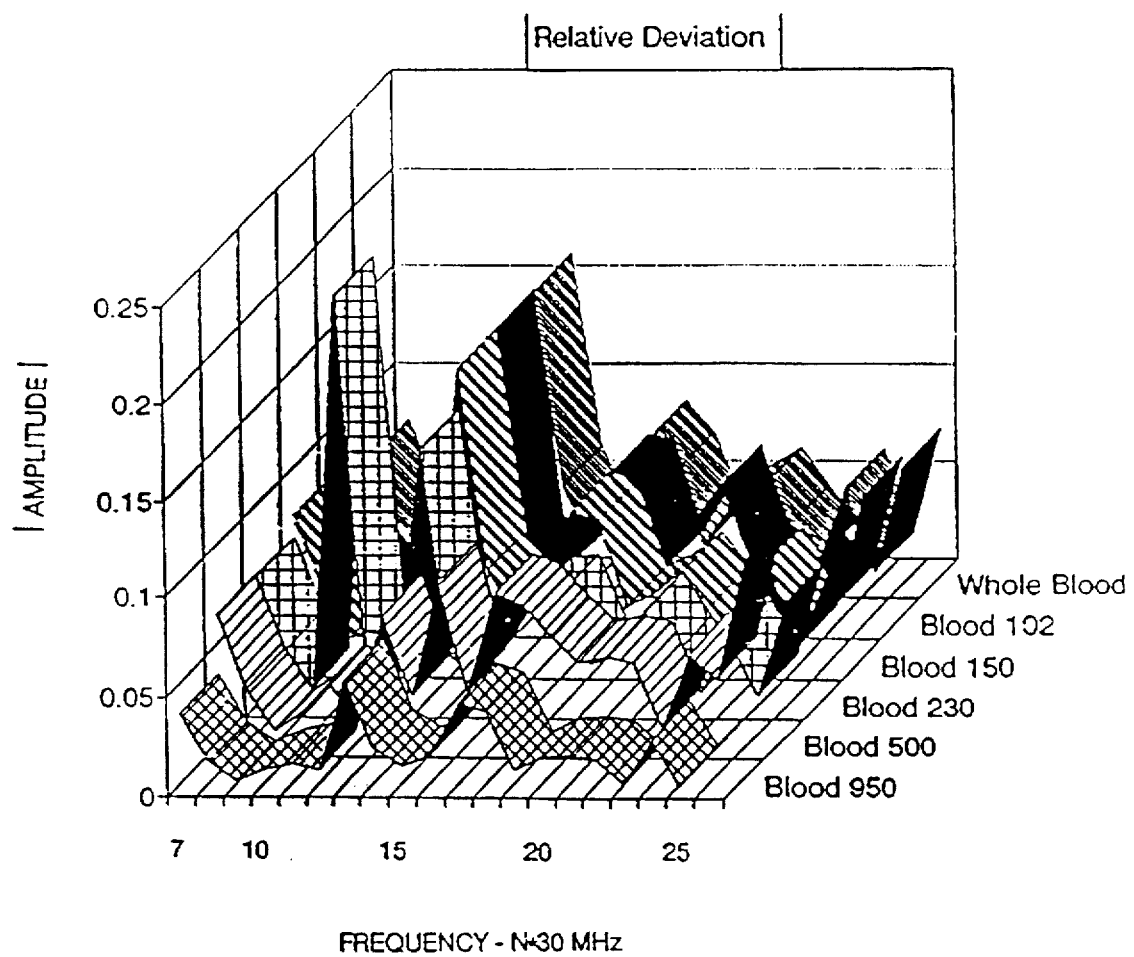

FIGS. 4A and 4B represent multiple averaged in-vitro data obtained with the system of FIGS. 1 and 2, using as a test specimen whole blood (e.g., red blood cells) to which glucose or lactose or sucrose or urea or NaCl was added as a test chemical. The test cells were compared to a calibrated cell that contained only red blood cells. FIG. 4C represents similar data for whole sheep's blood (e.g., no glucose), and for sheep's blood with various concentrations of glucose, where the nomenclature "Blood 102" denotes 102 mg-% or 102 mg per dL glucose. Typically, a healthy human has perhaps 80–120 mg % glucose, while a diabetic has 200–400 mg-% glucose. The vertical axis in FIG. 4C represents the vector amplitude the return signal, taking into account magnitude and phase. The horizontal axis represents harmonics of a 30 MHz source frequency, the first harmonic being at 210 MHz.

To minimize probe-related variables, the specimens in FIGS. 4A, 4B and 4C were tested using parallel plate capacitive cells. These cells comprised two dielectric substrates having a relative permittivity approximating that of water ($\approx 80$), with an electrode surface baked onto each substrate. The test substance was placed in a chamber between the substrates.

The varying degree of signal amplitude shown in FIGS. 4A, 4B, and 4B are termed "spectral signatures". What is depicted is the difference in amplitude between the calibrated cell (analogous to the use of the calibration unit 66 in FIG. 2) and the test specimen (analogous to the use of probes 6 and specimen 4 in FIG. 1). These data indicate that the system of FIGS. 1 and 2 may be used to discern the presence of a target chemical within a test specimen or sample.

A preferred application is the detection of excess glucose in a user's blood, e.g., within the specimen. Because the present invention operates non-invasively, it suffices for the user to press his or her finger against the probe pair 6, as shown in FIG. 1. In response to the high frequency, high harmonic content signal from transmitter 16, chemicals within the specimen can recognizably cause energy transfer of certain spectral components of the transmitted source signal. It is hypothesized that within the specimen, the target chemical glucose interacts with the lipid bilayer and/or red blood cell membranes.

Thus, in the presence of frequency components from the signal transmitted via probes 6, the glucose seems to bring about non-linear intermodulation or mixing of frequency components, possibly due to a non-linear dielectric phenomenon involving capacitance associated with glucose. Using the system of FIGS. 1 and 2, a diabetic user may rapidly obtain glucose concentration level information. Signal processing by unit 18 would, essentially in real time, provide glucose level information on display unit 20.

Of course other target chemicals may also be detected, including for example fructose, galactose, alcohol. For example, a system according to what is disclosed herein may be used to sense alcohol in a motorist's system, either by a motorist before attempting to drive, or by a police officer attempting to determine whether an individual is under the influence of alcohol.

Because the disclosed system of FIGS. 1 and 2 appears to be sensitive to boundary conditions at a lipid bilayer membrane, disruptions to such boundary conditions may be detected by a spectral signature. Thus, the presence of glucose in varying amounts at a membrane may be detected.

In a different utility, however, trauma to a specimen that interferes with such boundary conditions may also be detected, primarily for the purpose of providing medical treatment. For example victims of electrocution may received localized injuries, for example on an arm. Unless the injury sites are promptly treated by the injection of certain medication that is potentially rather toxic, the victim will lose the injured limb or die. Use of the invention disclosed herein would permit diagnosis of such injury sites, and quantizing the injury to facilitate prompt and accurate medical treatment.

Subsequent to the invention described with reference to FIGS. 1–4B, applicants came to appreciate the role that changing electrolyte concentrations can have upon glucose concentration measurements in blood specimens. Applicants further discovered that it is possible to improve analysis for a desired chemical by reducing the effects upon such analysis of varying concentrations of other substances in the specimen.

Figure 5A:
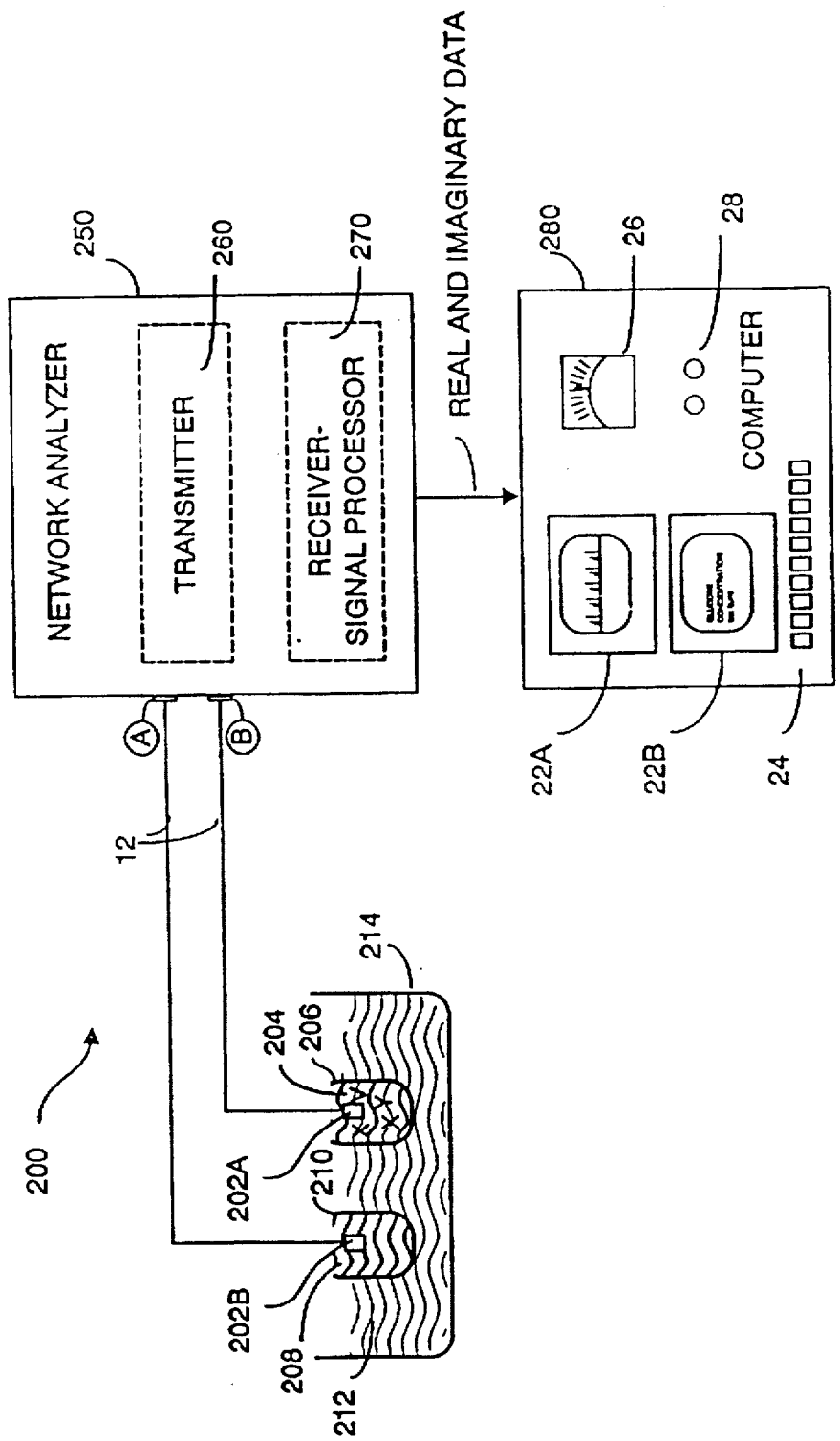
FIG. 5A depicts an in-vitro application of a radio frequency spectroscopy system with enhanced analysis sensitivity, according to the present invention.
Figure 5B:
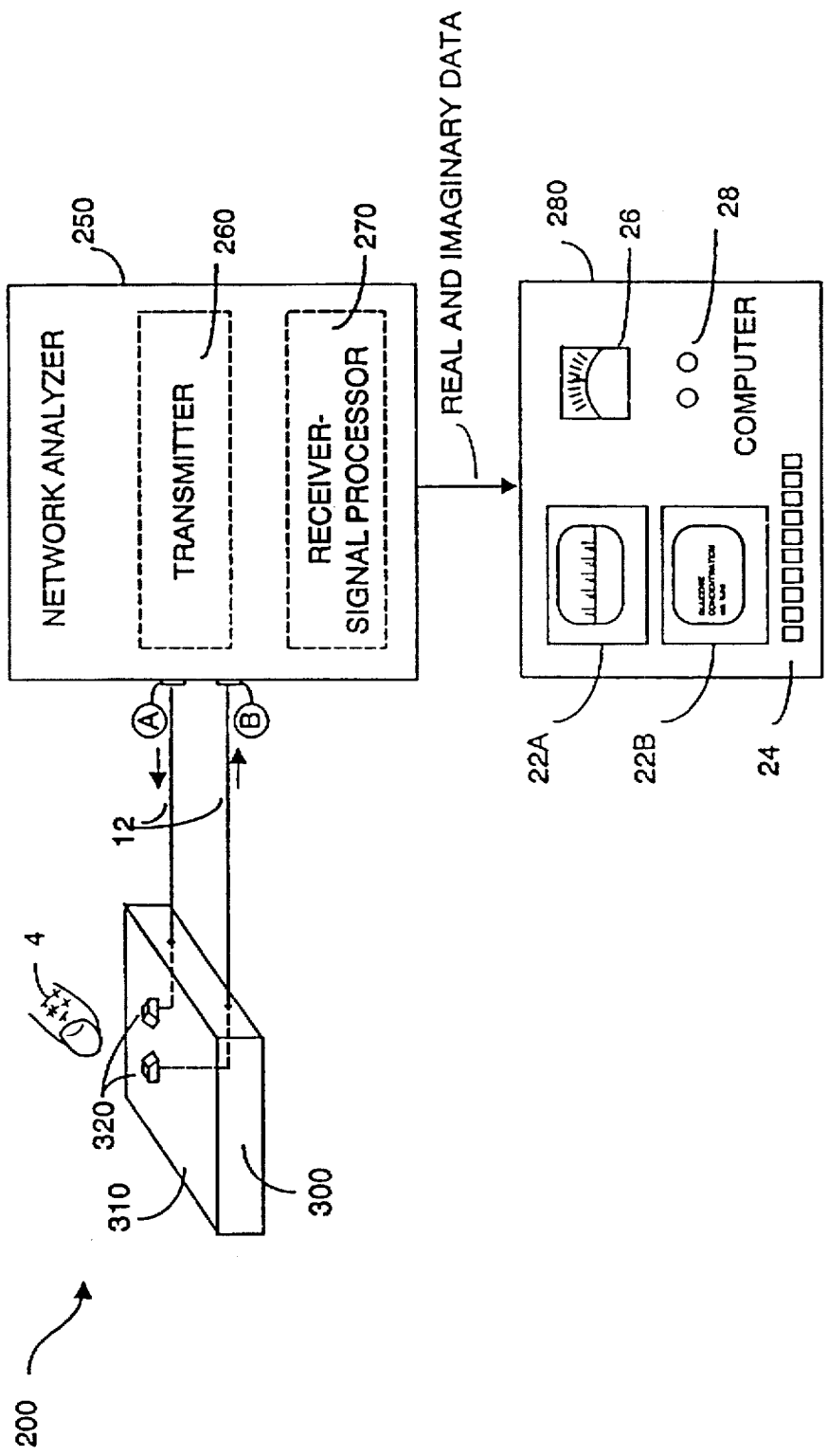
FIG. 5B depicts an in-vivo application of a radio frequency spectroscopy system with enhanced analysis sensitivity, according to the present invention.

FIGS. 5A and 5B respectively show in-vitro and in-vivo applications of improved analysis using a system 200, according to the present invention. In FIG. 5A, preferably two probes 202A, 202B are coupled by short lengths of coaxial cable 12 to ports A and B of a frequency generator and analyzer system 250. In general, the transmitted signal is sent from port A or port B, and a portion of the transmitted signal is reflected by the specimen back into the transmitting port. In transmission mode (e.g., FIG. 5B), port B returns the fraction of the signal transmitted via port A through the subject's finger.

In the embodiments of FIGS. 5A and 5B, cables 12 preferably are 20 cm or less lengths of coaxial cable, and probes 202A, 202B preferably are Hewlett Packard HP 85075B dielectric probes. These probes are coaxial in construction, having an outer diameter of perhaps 2 cm and a probe length of perhaps 3.8 cm. The probes have a center conductor that is surrounded by a groundplane sheath at the probe tip. However, other cable couplings and probes could also be used.

As will be described, system 250 includes a transmitter unit 260 that can output discrete sinusoidal waveforms that are spaced-apart in frequencies linearly or logarithmically in user-selectable steps. Further, the output frequencies are stepped between user-selectable lowermost and uppermost frequencies $f_l$ and $f_u$, respectively. In the preferred embodiments, $f_l$ was about 300 KHz, $f_u$ was about 3 GHz, with approximately 801 linearly-spaced frequencies output between $f_l$ and $f_u$. Applicants believe, however, that an $f_u$ of about 5 GHz would also be useful to the present invention. In the preferred embodiment, system 250 was implemented using a commercially available Hewlett Packard HP 8753A network analyzer with an HP 85046A S-parameter test set. However, other systems implementing similar functions could be used instead.

System 270 further contains a receiver and signal processor unit 270 that analyzes waveforms associated with signals transmitted by and/or at least partially reflected back to system 270. The waveforms under analysis are associated with discrete user-programmable frequencies. The analysis can examine real and imaginary components of these waveforms, including complex (e.g., having real and imaginary components) reflection coefficient data. These various data are signal processed by unit 270 to provide information including complex impedance magnitude (Z), phase shift, and/or permittivity.

Among the electrolytes, NaCl has the most significant influence on measurements, in that its normal concentration range in the human body is 135–145 mM (millimolar), whereas KCl, by example, is only abut 4–10 mM. Substances such as urea were confirmed to not influence glucose measurements, probably because urea has a molecular size that is one-third that of glucose, and has a physiologically controlled concentration ranging from 5–40 mg/dl. The range of glucose in a human normally is about 50 mg/dl (or mg %) to 150 mg/dl, and can reach about 500 mg/dl in a diabetic.

In FIG. 5A, probe 202 contacts a specimen of interest 204, perhaps about 40 ml, retained within a beaker or receptacle 206 whose volume is perhaps 100 ml. Specimen 204 includes a chemical of interest denoted X, as well as one or more other substances, denoted collectively Y. In a preferred embodiment, specimen 204 is a bodily fluid, for example blood, X is glucose (whose presence and/or concentration is to be determined), and Y may include varying concentrations of blood electrolytes such as NaCl, Na$_2$HPO$_4$, KCl, and KH$_2$PO$_4$, as well as proteins and lipids.

Although large concentrations of proteins and lipids are also found in blood, the human body maintains relatively tight control over variations in such substances, and thus their presence appears not to substantially affect measurements according to the present invention.

In an industrial application, specimen 204 may be a solution in which X and Y represent different chemicals, in which the presence and/or concentration of X is to be discerned, for example to confirm quality control of the production of solution 204.

A second container 210 into which probe 202B is inserted contains a test or control solution 208 that intentionally lacks at least one chemical found in specimen 204. Both specimens preferably are retained at a same temperature by partially immersing containers 206, 210 in a preferably constant temperature bath 212 maintained within a larger beaker or container 214.

In FIG. 5A, analyzer unit 250 is operated with signals at ports A and B in a reflectance mode, e.g., in which signals transmitted out of each port are at least partially reflected back into the ports by the respective specimens. From the real and imaginary components of the reflected signal data, useful information as to the presence and concentration of at least one chemical in solution 204 may be determined, according to the present invention.

Applicants have discovered that the real and imaginary components of the reflected signals can be affected by the nature and content of the specimen solutions in the immediate vicinity of the tips of the probes. What is believed to occur is that fringing fields extend from the center conductor of the preferably dielectric probes to the surrounding ground plane. As the properties of the specimen solutions change, e.g., due to the presence and concentration of one or more chemicals or other substances therein, the fringing field is affected. The alterations to the fringing field in turn affect the reflected signals being returned to ports A and/or B of the analyzer unit 250.

The complex data gathered and processed by unit 250 is coupled as input to a computer unit 280 for further processing. If desired, computer unit 280 may include any or all of the output indicators 22A, 22B, 24, 26, 28 described earlier with respect to FIG. 1, as well as any other output indicator (s) that may be desired.

Computer unit 280 may be a personal computer executing a software routine permitting conversion of the real and imaginary data it receives into forms including the magnitude of the effective complex impedance Z presented by the specimen, phase shift between signals transmitted and at least partially reflected back by the specimen, effective permittivity, and the like.

In the preferred embodiment, computer 280 executed Excel spreadsheet software to convert the incoming complex data into more useful form. A modified Bao procedure was adopted, in which complex impedance (Z) is determined from the complex reflection coefficient (Γ) at the interface between the flat end of a probe, e.g., 202A, and a specimen solution, e.g., 204.

$$Z = Z_o \frac{1 + \Gamma}{1 - \Gamma} \quad (1)$$

The characteristic impedance $Z_o$ of coaxial line 12 may be calculated from the relationship:

$$Z_o = 377 \sqrt{\frac{\mu_R}{\epsilon_R}} \cdot \frac{\ln \frac{b}{a}}{2 * \pi} \quad (2)$$

in which 377 represents impedance of air, b is the outside diameter of the probe, a is the diameter of the inner lead on the probe, $\mu_R$ is the permeability of air, and $\epsilon_R$ is the permittivity of Teflon.

However, measured reflection coefficient from analyzer 250 is not necessarily an accurate representation of Γ, due to errors caused by the container 206, the coaxial line 12, and connectors at port A, for example. The Bao procedure reduces these errors, using a calibration procedure based on a linear assumption. This assumption and the values collected from the calibration procedure give rise to a matrix derivation $$\epsilon = \frac{A_1 P_m - A_2}{A_3 - P_m} \quad (3)$$

in which $A_x$ is a frequency dependent complex constant related to a scattering matrix.

During the course of experimentation, applicants realized that if analyzer 250 were calibrated with port connectors and coaxial cables 12 attached, the analyzer output would be Γ, whereupon use of the Bao matrix procedure would be unnecessary.

Thus, while equation (1) is valid, its real and imaginary components should be separated to be effectively used by computer 280 during execution of a data processing routine, e.g., an Excel spreadsheet program.

Consider then equations (4) and (5), in which ρ is the complex reflection coefficient output from analyzer 250:

$$Z_{Real} = \frac{Z_o(1 - \rho_{Real}^2 - \rho_{Imag}^2)}{(1 - \rho_{Real})^2 + \rho_{Imag}^2} \quad (4)$$

$$Z_{Imag} = \frac{Z_o(2 \cdot \rho_{Imag})}{(1 - \rho_{Real})^2 + \rho_{Imag}^2} \quad (5)$$

$$Z_{Mag} = \sqrt{Z_{Real}^2 + Z_{Imag}^2} \quad (6)$$

Euler's formula is used as shown in equations (6) and (7) to convert equations (4) and (5) to the more commonly encountered impedance magnitude and phase quantities:

$$Z_\theta = \tan^{-1} \frac{Z_{Imag}}{Z_{Real}} \quad (7)$$

Referring back to FIG. 5A, the various analytes in a blood specimen, especially small ion electrolytes (also called blood electrolytes), can measurably affect the impedance and phase angle. In an application in which glucose concentration is to be determined, what actually may be measured with system 200 is the effect of glucose, e.g., X in FIG. 5A, upon ions or water dipoles in the specimen solution 204. Applicants have discovered at certain cross-over frequencies output by system 250, the effects of other substances Y in the specimen 204, including electrolytes, can be reduced or nulled-out. For example, at a cross-over frequency of about 2.5 GHz, the concentration effects of NaCl and most probably other blood electrolytes in a blood specimen are nulled-out, without degrading glucose concentration measurements. In an analytical scheme in which N equations would have to be solved for N unknowns, the ability to null-out electrolyte concentrations effectively reduces the number of variables and thus the number of equations that must be solved. The end result is that glucose concentration can be determined with higher specificity and confidence. Further, as described later herein, phase shift measurements (e.g., comparison between transmitted and reflected signals) over a wide frequency regime provide a surprisingly linear response to electrolyte concentration. The phase shift data can then be used to compensate for NaCl concentration contributions to total impedance measurements made at frequencies lower than the 2.5 GHz cross-over frequency.

When generator 260 outputs frequencies greater than perhaps 1 GHz or so, the specimen impedance magnitude appears to be primarily a function of the ability of water dipoles to respond in the presence of the resultant oscillating field in the vicinity of the probe(s). At output frequencies less than perhaps 500 MHz, impedance magnitude seems to be more a function of ionic response to the oscillating field in the vicinity of the probe(s). Within a blood specimen, NaCl is an important source of such ions. At inbetween frequencies, the impedance function transitions.

Below approximately 500 MHz, glucose in the specimen solution appears to impede ionic mobility in responding to the oscillating field, and thus the effective impedance increases. For example, between about 10 MHz and 100 MHz, impedance change due to NaCl concentration changes in the specimen are substantially stronger than impedance changes due to concentration changes in glucose.

Applicants have discovered that at test frequencies below about 1 GHz, increasing concentrations of NaCl decrease impedance magnitude ("Z"), and that at a cross-over frequency of about 2.5 GHz, impedance measurements are sensitive to glucose concentration but insensitive to electrolyte concentration. Further, applicants have learned that over a wide frequency regime, phase shift increases linearly with increasing NaCl concentration, with little or no effect due to changing glucose and/or albumin concentration. Thus, it appears that at higher frequencies (e.g., above 1.5 GHz or so), larger molecules simply do not respond sufficiently rapidly to meaningfully influence phase shift measurements. By contrast, electrolytes, including NaCl, have small ions that can respond measurably with respect to phase shift measurements. As described herein, collectively, these discoveries provide measurement protocols to reliably and with specificity determine glucose concentration, despite the presence of electrolytes of varying concentrations.

In FIG. 5B, a non-invasive system for in-vivo testing is depicted. In this embodiment, network analyzer or system 250, and computer system 280 may be identical to what was described with respect to FIG. 5A. However, an electrode assembly 310 comprising two metallic probes 320 spaced-apart perhaps 2.5 cm on a substrate 300 is used. Substrate 300 may be a sheet of single-sided copper clad printed circuit board measuring perhaps 5 cm×7.5 cm. Electrodes 320 preferably are made from brass and are about 0.6 cm tall, 0.6 cm wide, and about 1.2 cm in length. Spaced-apart faces of the probes define a surface slanted at about 45°. Each conductive electrode 320 is connected to one coaxial cable 12. The finger 4 of a subject to be tested for glucose concentration, for example, is pressed against the slanted surfaces of the probes, thus completing an electrical circuit with coaxial cables 12, and thus ports A and B of analyzer system 250. It is understood in FIG. 5B, that port A will receive back a portion of the transmitted signal as a reflected signal. Port B will receive that portion of the transmitted signal that propagates through the specimen tissue.

In practice, probe assembly 310 provides enhanced signal to noise ratio, and improved repeatability relative to other probe designs, including the probe assembly depicted in FIG. 1. Reliable data have been obtained with probe assembly 310, typically in the frequency range of about 1 MHz to about 3 GHz. It will be appreciated that the configuration of FIG. 5B is especially useful to laypersons, including suspected and actual diabetics, who wish to monitor their own blood chemistry, especially glucose concentration levels.

Figure 6A:
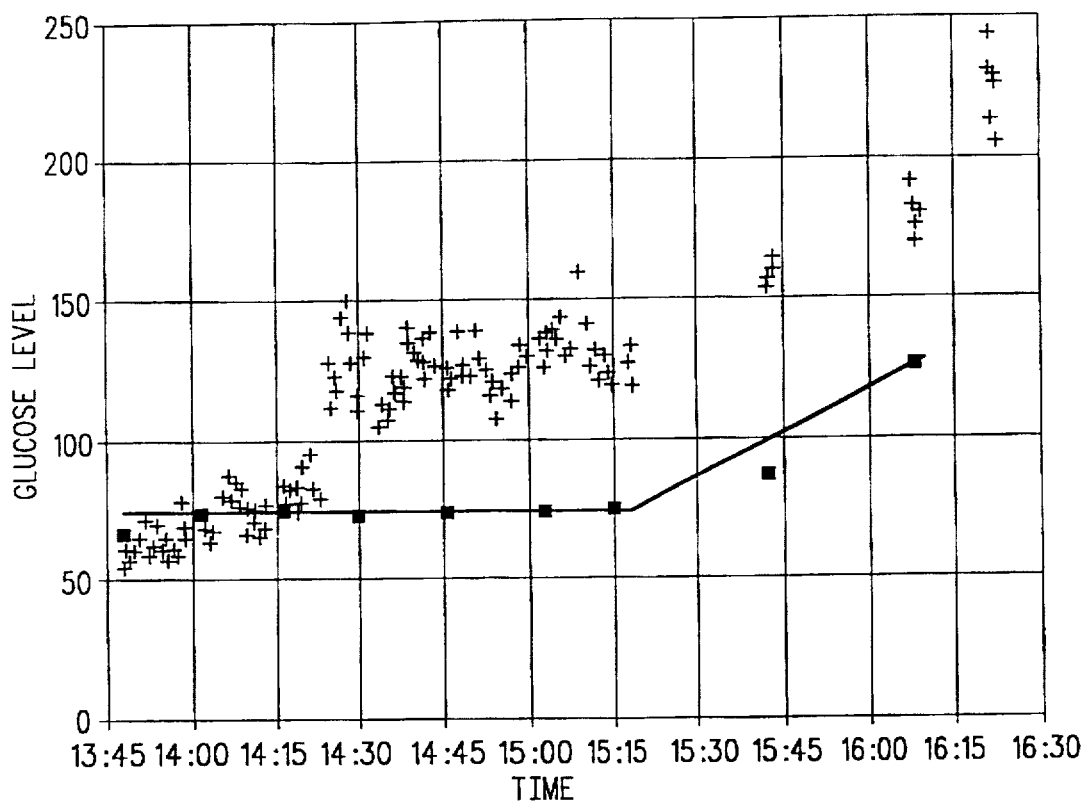
FIG. 6A compares non-invasive and invasive impedance magnitude test data for a subject, using a test configuration according to FIG. 5B.
Figure 6B:
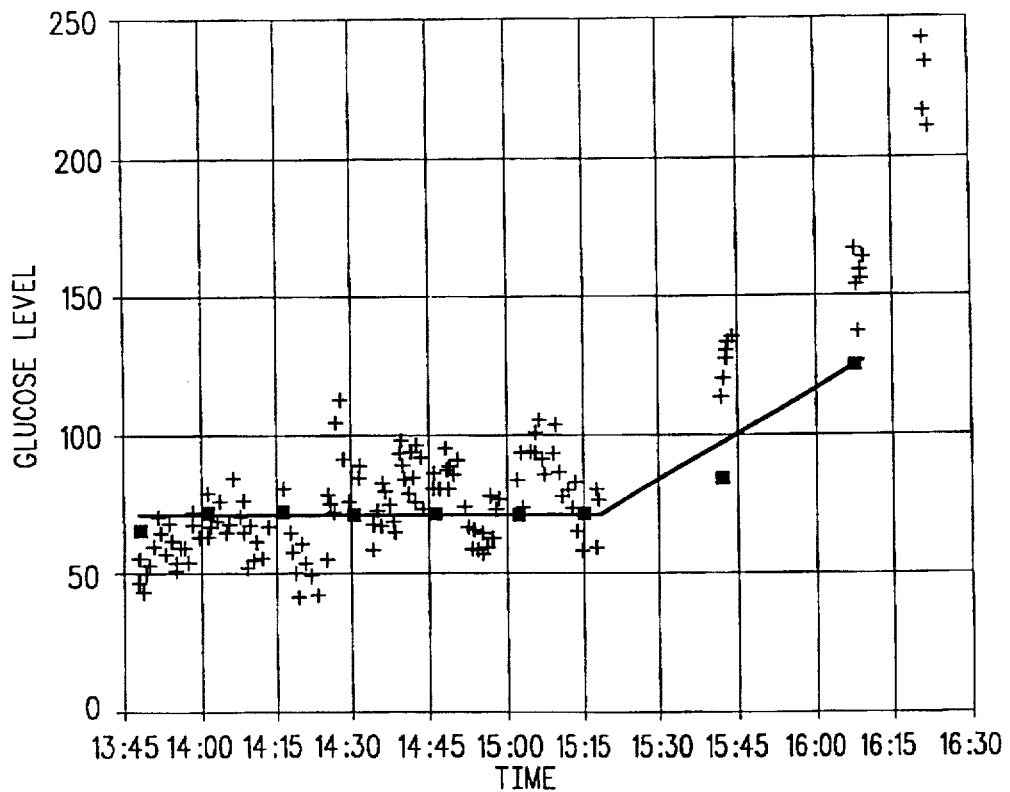
FIG. 6B shows correction for electrolyte dilution for the sam data shown in FIG. 6A.

FIGS. 6A and 6B plot predicted and actual glucose concentration against time, for non-invasively obtained test data (shown by "plus signs") and for invasively obtained data (shown by "boxes"). Both figures depict the same experiment in which a human subject drank water at 14:00 hours (2:00 P.M.) and ate food at 15:15 hours (3:15 P.M.) The non-invasive test data were obtained using finger probes 320 such as shown in FIG. 5B, whereas invasive test data were obtained from actual blood samples from the subject.

Approximately 101 separate frequencies were used to obtain raw data during the experiment. FIG. 6A depicts non-invasive predicted glucose concentration based upon impedance and phase data taken at about 17 MHz. The impedance and phase data were then converted into predicted glucose concentration data using an algorithm.

In FIG. 6A, predicted glucose concentration shows an increase at about 14:20 hours, apparently corresponding to the subject's intake of water. In essence, the water has diluted electrolyte concentration in the subject, which has caused predicted glucose concentration to offset vertically, erroneously, by some 50 units. After 15:15 hours, the predicted glucose level rises, which represents the subject's intake of food. Note, however, that the same 50 unit vertical offset is still present.

Using mathematical regression analysis to examine data for the approximately 101 frequencies used, applicants realized that non-invasive phase shift data taken at 103 MHz would provide a correction for the 50 unit error offset in non-invasive glucose predictions taken at 17 MHz.

FIG. 6B shows the same experiment, now plotted with correction data taken at 103 MHz, in which "plus signs" depict predicted non-invasive glucose concentration data from the subject using 17 MHz transmission-mode impedance magnitude data as corrected by the 103 MHz phase shift data. Clearly the use of the higher frequency phase shift correction has largely compensated for the 50 unit offset (present in FIG. 6A but not in FIG. 6B), resulting from water dilution of electrolytes.

In general, FIG. 6B shows close agreement between actual invasively measured glucose concentration, and non-invasively predicted glucose concentration. Although not fully appreciated by applicants at the time the subject experiment was conducted, it appears that the 103 MHz phase shift data provides a good measure of electrolyte concentration including the effects of electrolyte dilution. At 103 MHz, small ion electrolytes including NaCl could respond to the oscillating field, whereas larger glucose molecules could not, and thus would not substantially influence the measurement. By contrast, the 17 MHz data provided a measure of glucose and electrolyte concentration, which data when compensated for by the 103 MHz electrolyte concentration data provided a truer measure of predicted glucose concentration.

Collectively, FIGS. 6A and 6B suggest the wisdom of using data obtained at different frequencies or frequency regimes (e.g., 17 MHz and 103 MHz in this example), to measure different parameters (e.g., total impedance, and phase shift), to provide a measure of compensation to more accurately arrive at the desired data (e.g., glucose concentration) with a greater specificity confidence level.

Figure 7A:
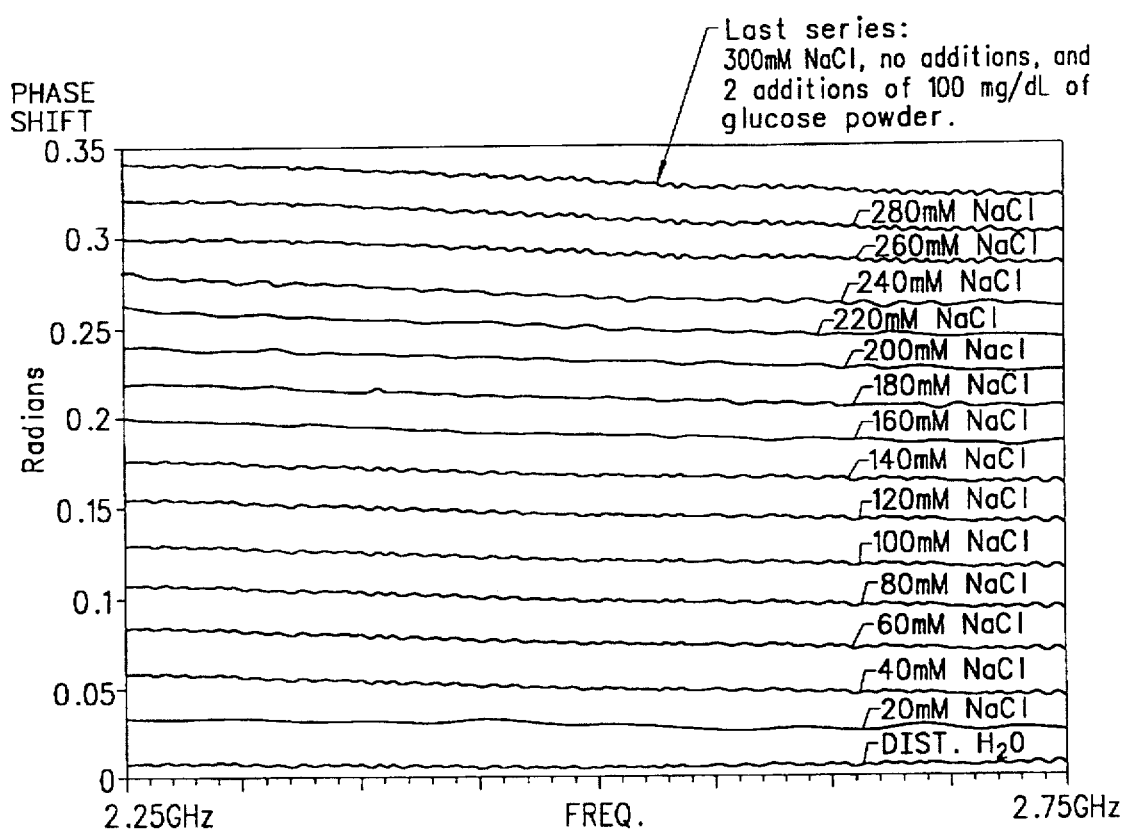
FIG. 7A depicts linear relationship between electrolyte concentration and phase shift, independently of glucose concentration.

FIG. 7A depicts the startlingly linear relationship observed by applicants between NaCl concentration and phase shift between transmitted and reflected signal at a specimen. In FIG. 7A, various frequencies between 2.25 GHz and 2.75 GHz were used, phase difference was between two probes, e.g., probes 202A/B in FIG. 5A. The experiment began with distilled water, which at shown at the bottom of the graph had 0 radian phase shift. Adding increments of 20 mM NaCl to the distilled water showed a very linear relationship: higher NaCl concentration increased the measured phase shift rather linearly. At the very top of the graph, data were obtained first for 300 nM NaCl, after which two 100 mg/dL of glucose powder was added to the salt water solution. As seen, in the 2.25 GHz to 2.75 GHz frequency regime displayed, changing glucose concentration (indeed a rather substantial change in glucose concentration) did not affect phase shift measurements, whereas changing NaCl concentration produced a linear change in measurable phase shift.

Figure 7B:
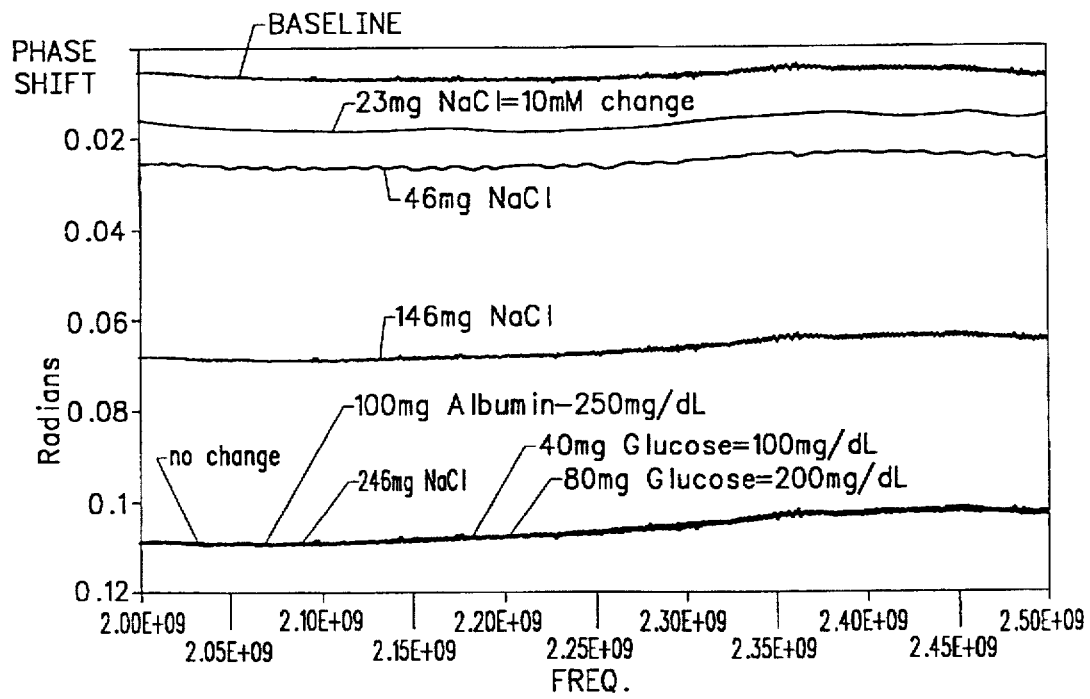
FIG. 7B depicts linear relationship between electrolyte concentration and phase shift in a PBS solution, independently of glucose and/or albumin concentration.

FIG. 7B is averaged phase shift data obtained with two probes, using frequencies ranging from 2.0 GHz to 2.5 GHz, in which varying concentrations of NaCl, glucose, and albumin were added to a baseline solution of phosphate buffered saline ("PBS"). PBS was used in that it mimics the electrolyte environment of blood well, without proteins or other substances being present in the solution.

Consistent with the findings of FIGS. 6A and 6B, increasing NaCl concentration increased phase shift in a linear fashion in FIG. 7B. Of special significance, however, is the bottommost portion of the graph, which corresponds to a phase shift of about 0.11 radians for a 246 mg NaCl solution. This data line remained constant, even when 40 mg (100 mg/dl) and then 80 mg (200 mg/dl) glucose were added, and even when 100 mg (250 mg/dl) albumin was further added. The data of FIG. 7B demonstrates that the linear phase shift measurable for varying electrolyte concentration is not meaningfully influenced by glucose concentration and/or albumin concentration.

Figure 7C:
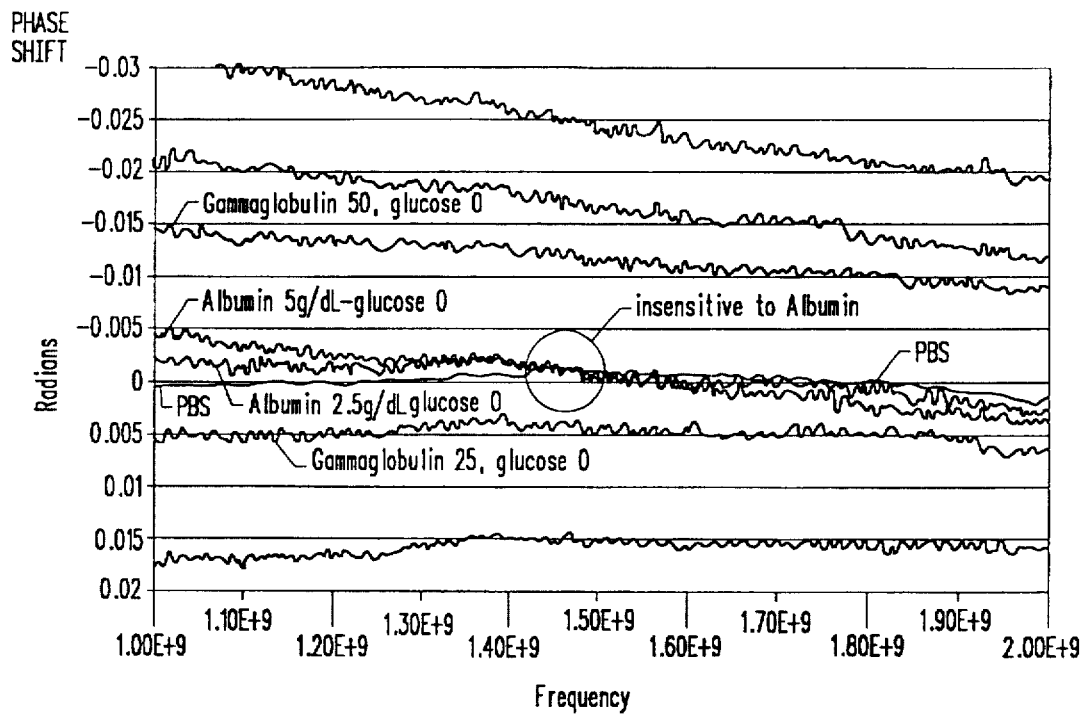
FIG. 7C demonstrates how improved specificity for a target analyte can be realized by including measurements that are insensitive to a constituent in the specimen, for example, phase shift measurements at 1.5 GHz to null-out albumin concentration.

FIG. 7C is a composite graph that demonstrates that a cross-over frequency of about 1.5 GHz renders phase shift measurements highly insensitive to varying albumin concentrations in a PBS solution. In FIG. 7C, the bottommost trace at about 0.017 radians represents phase shift caused by changing concentration of gamma globulin by 5 g/dl, and the trace at 0.005 radians represents phase shift caused by changing concentration of gamma globulin by 2.5 g/dl. The uppermost trace in FIG. 7C represents phase shift due to intralipids at 1.4 g/dl concentration, the trace at −0.02 radians represents a different analyte with glucose, not herein relevant, and the −0.015 phase shift represents intralipids at 0.7 g/dl concentration. Of special interest are the three tracelines centered about 0 radian phase shift. The trace at −0.005 radians represents albumin at 5 g/dl concentration, the trace at about −0.0025 radians represents albumin concentration of about 2.5 g/dl, and the trace at 0 phase shift is the baseline PBS. The various concentrations above noted are substantially greater in magnitude than variations that would ever occur in a human being. Note that at a frequency of about 1.5 GHz, phase shift is substantially insensitive to albumin concentration level. Thus, by measuring different characteristics associated with a specimen at different frequencies or over different frequency regimes, the effects of various constituents can be nulled-out. In the example of FIG. 7C, greater measurement specificity is attained for a desired analyte, e.g., glucose, in the presence of other substances, e.g., albumin.

Figure 7D:
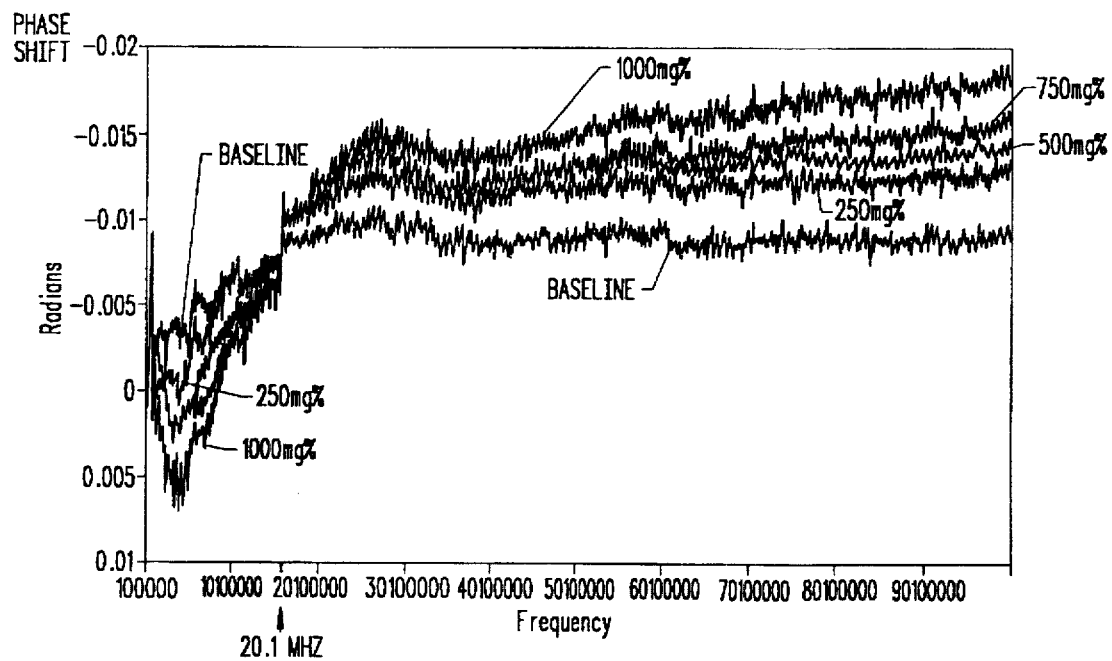
FIG. 7D depicts a phase cross-over frequency of about 20.1 MHz whereat phase shift data is independent of glucose concentration.

FIG. 7D depicts phase shift data between about 300 KHz and 100 MHz for changing concentrations of glucose, the glucose being added to sheep blood in increments of 250 mg %. It is seen that at about 20.1 MHz, phase shift data is insensitive to glucose concentration.

Figure 8A:
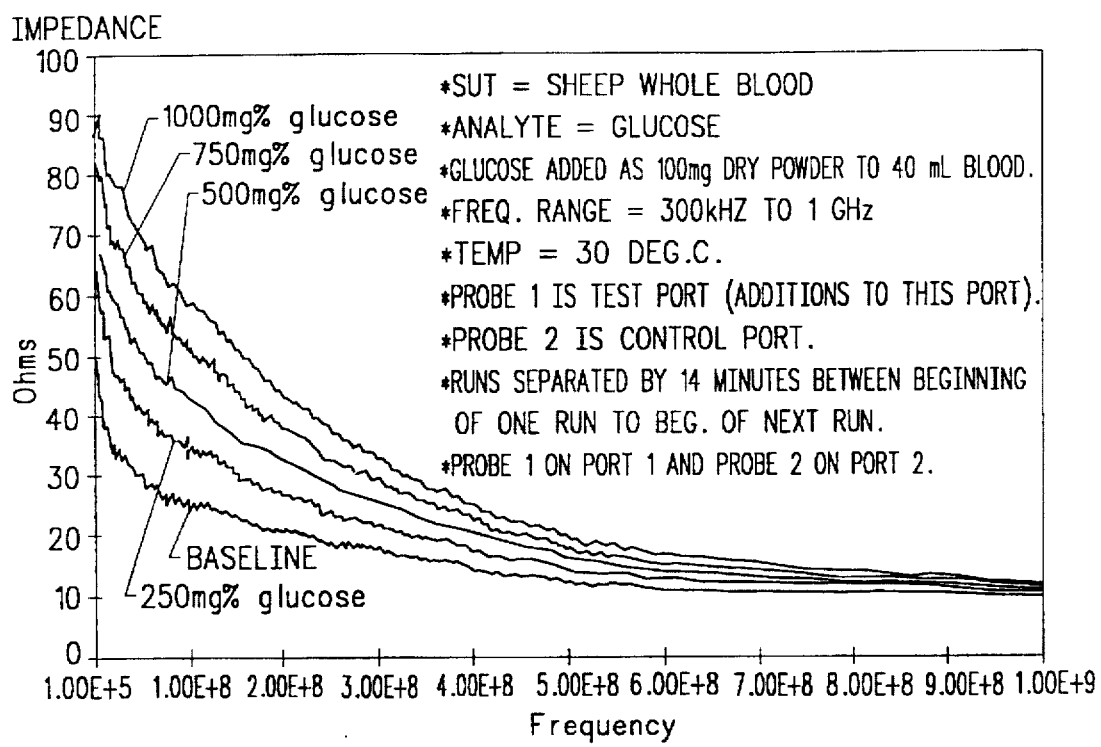
FIG. 8A depicts the increase in impedance measured from about 0.1 MHz to about 1 GHz with increasing glucose concentration.

FIG. 8A depicts magnitude impedance data measured in a sheep blood baseline solution, for various glucose concentrations, using frequencies ranging from 0.3 MHz to 1.0 GHz. Over this extremely wide frequency regime, increasing concentrations of glucose increase impedance. The relative change of glucose concentration upon impedance is greater at frequencies lower than about 0.5 GHz, no doubt because at lower frequencies the large glucose molecules exert greater hinderance upon ion movement.

In general, applicants have learned to appreciate that impedance measurement accuracy is higher at low frequencies than at higher frequencies. Thus, as will be seen, impedance measurements at 2.5 GHz can provide a measure of glucose concentration nulling-out NaCl and other electrolyte concentrations, the equipment measurement sensitivity is substantial less than at say 100 MHz. For example, a measurement sensitivity of 0.1 Ω is a good design goal. However, at 2.5 GHz, impedance magnitude sensitivity will be about ½5th the sensitivity at 100 MHz. Thus, as described herein, a recommended protocol will involve impedance and/or phase measurements in the GHz range, as well as measurements at much lower frequencies.

Figure 8B:
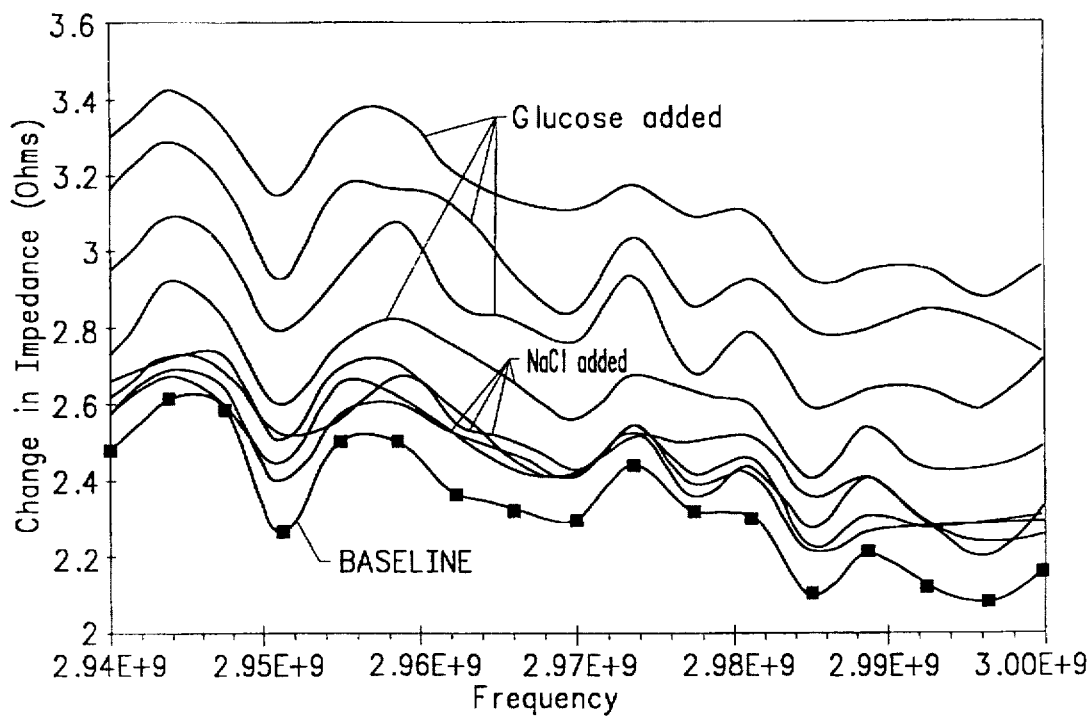
FIG. 8B depicts a frequency regime in which increasing NaCl and glucose concentrations increase impedance.

FIG. 8B depicts impedance change when a specimen of sheep's blood has glucose added, but relatively little change when concentrations of NaCl are added. The bottommost plot (with "boxes") is baseline sheep blood with a declotting agent. One addition of NaCl was then added (equivalent to change in concentration of 10 mM), and data taken at five minute intervals for the next five runs. During the last (uppermost) four runs, glucose was added. Glucose additions clearly increase the measured impedance. Note that, contrary to behavior at lower frequencies, adding NaCl in the 2.94 to 3 GHz regime actually increased impedance, probably due to an interaction of ions with water molecules.

Figure 8C:
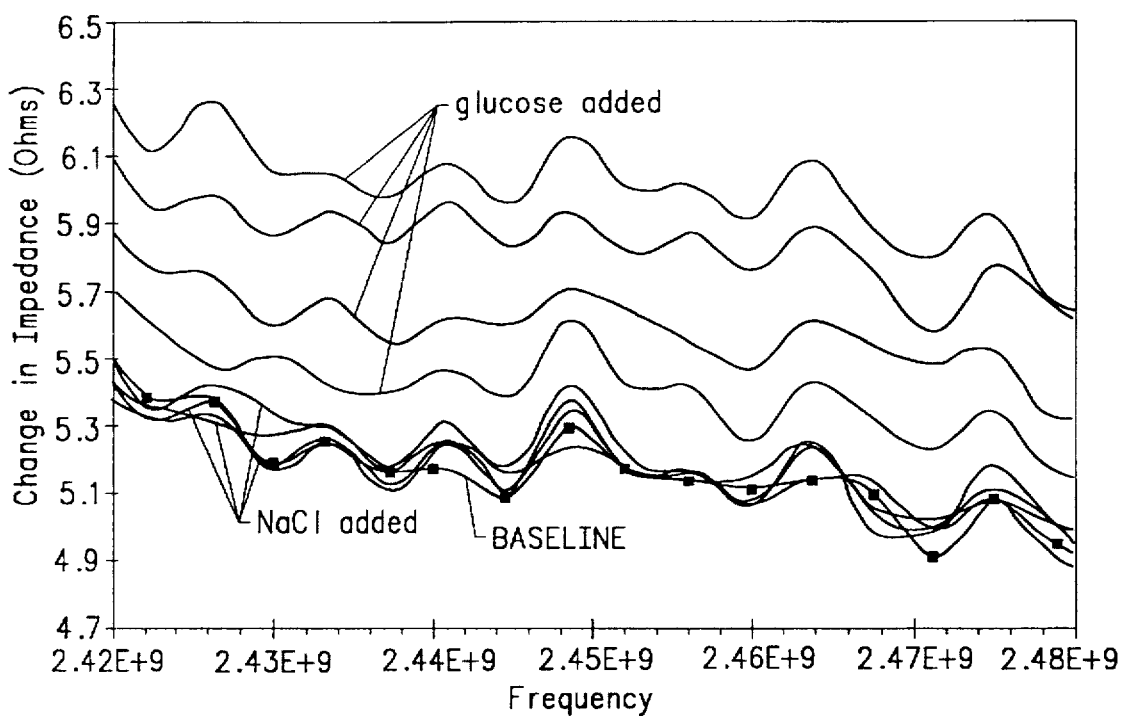
FIG. 8C depicts a frequency regime in which increasing NaCl concentration does not substantially affect impedance, but increasing glucose concentration increases impedance.

In FIG. 8C, impedance data were obtaining using frequencies ranging from about 2.42 GHz to about 2.48 GHz. Again, a baseline solution of sheep blood (drawn with "boxes") was used, into which one addition of NaCl was made, followed by four additions of glucose. For the NaCl additions, essentially no impedance change results in this frequency regime. However, the uppermost four runs, which represent addition of increasing concentrations of glucose, clearly increase impedance in this frequency regime. Thus, impedance measurements in a frequency regime of about 2.42 GHz to about 2.48 GHz are sensitive to glucose concentration, and are insensitive to NaCl and other small ion electrolyte concentrations. While sheep blood was used as the specimen, similar results are obtainable with human blood. Further, as noted earlier, the human body maintains tight homeostatic control over concentrations of most electrolytes, proteins and lipids within the blood.

Figure 8D:
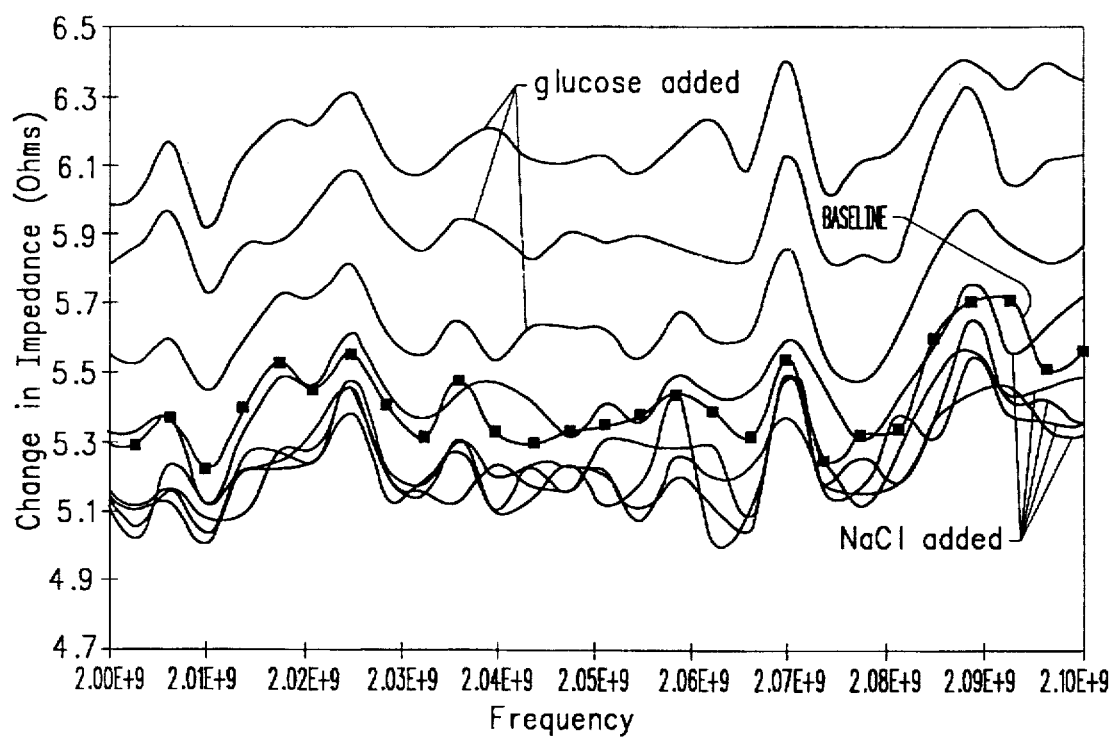
FIG. 8D depicts a 2.0 GHz to 2.1 GHz frequency regime in which increasing NaCl concentration decreases impedance, while increasing glucose concentration increases impedance reasonably linearly.

FIG. 8D depicts impedance data for a frequency regime of about 2 GHz to about 2.1 GHz for a baseline of sheep blood (drawn with "boxes"). In the bottommost runs, the addition of NaCl (10 mM concentrations increments) caused a decrease in impedance. However, in the uppermost four runs, additions of glucose clearly increased impedance in a linear fashion.

Figure 8E:
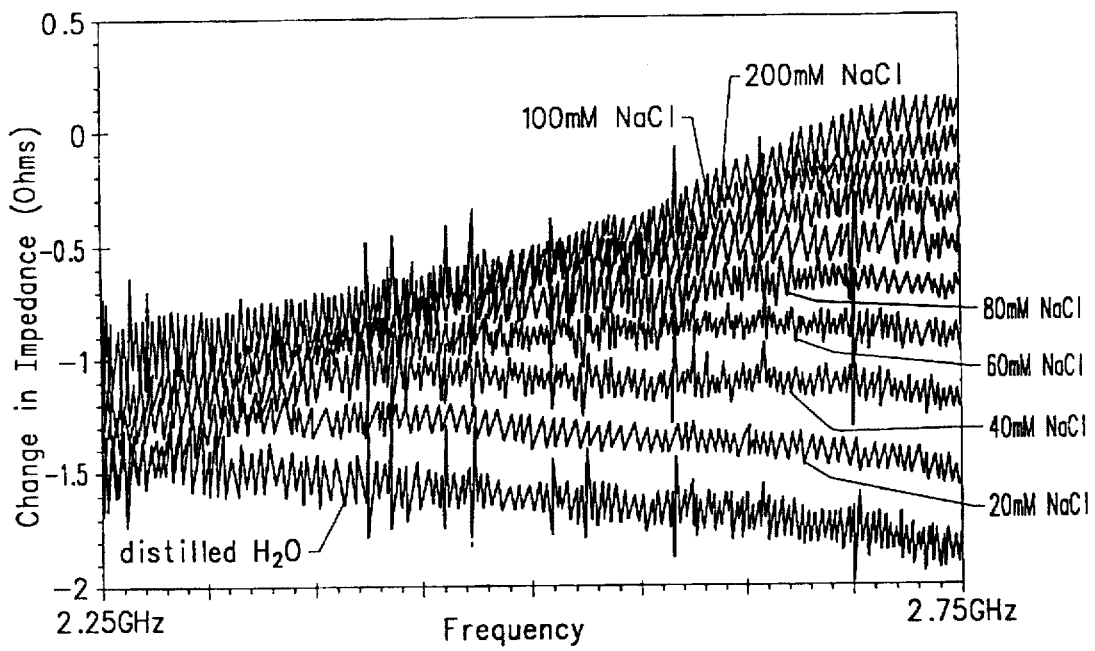
FIG. 8E depicts the non-linear behavior of impedance magnitude data over a 2.25 GHz to 2.75 GHz frequency regime as NaCl concentration is varied, according to the present invention.

FIG. 8E depicts impedance magnitude measurements made using frequencies ranging from about 2.25 GHz to 2.75 GHz, with a specimen of distilled water into which increasing concentrations of NaCl were added. The bottommost traces represent distilled water baseline data, and the remaining traces reflect increasing concentrations of NaCl, with the uppermost trace representing highest concentration (200 mM NaCl). Interestingly, the effect of increasing NaCl concentration upon impedance varies non-linearly with frequency. The right portion of FIG. 8E demonstrates that impedance increases with increasing NaCl concentration (a result opposite to what is encountered below about 1 GHz). By contrast, the left portion of FIG. 8E shows first an increase and then a decrease in impedance as NaCl concentration increases (e.g., as more Na or Cl ions are added to the test solution).

Figure 8F:
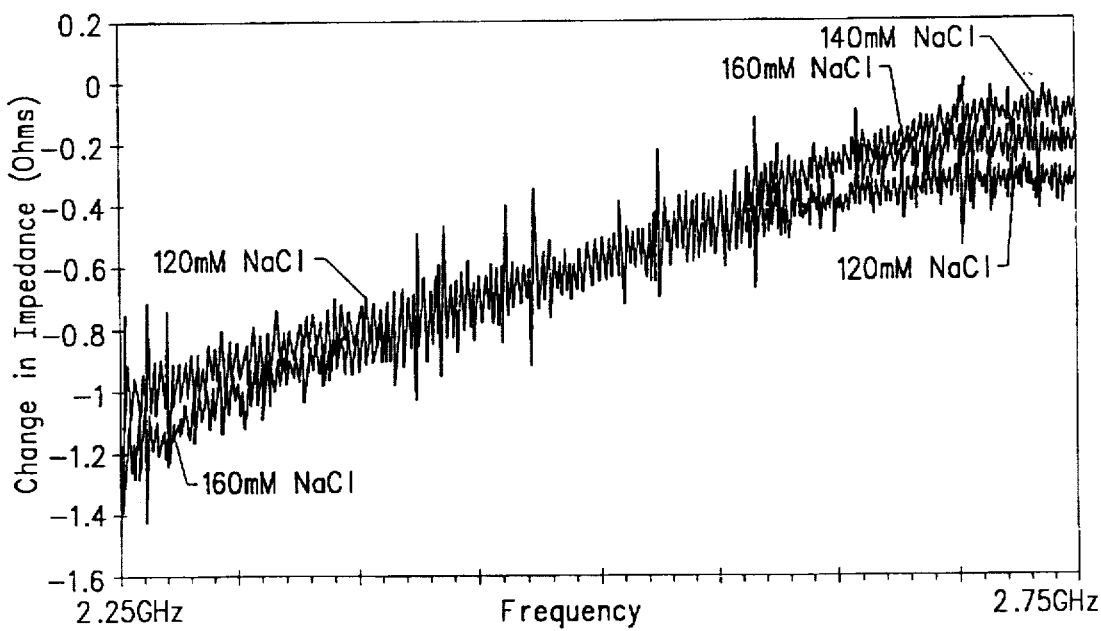
FIG. 8F depicts the existence of a cross-over frequency at about 2.5 GHz at which NaCl concentration effects upon measured impedance are nulled-out.

FIG. 8F demonstrates that use of a frequency of about 2.5 GHz can null-out essentially all changes in NaCl concentration upon impedance measurements. The data shown in FIG. 8F were gathered using a distilled water specimen into which increasing concentrations of NaCl were added. At the approximately 2.5 GHz cross-over frequency, all curves intersected, independently of NaCl concentration. Note that the NaCl concentrations used in FIG. 8F included the human physiological range of about 135 mM to 145 mM NaCl.

Figure 8G:
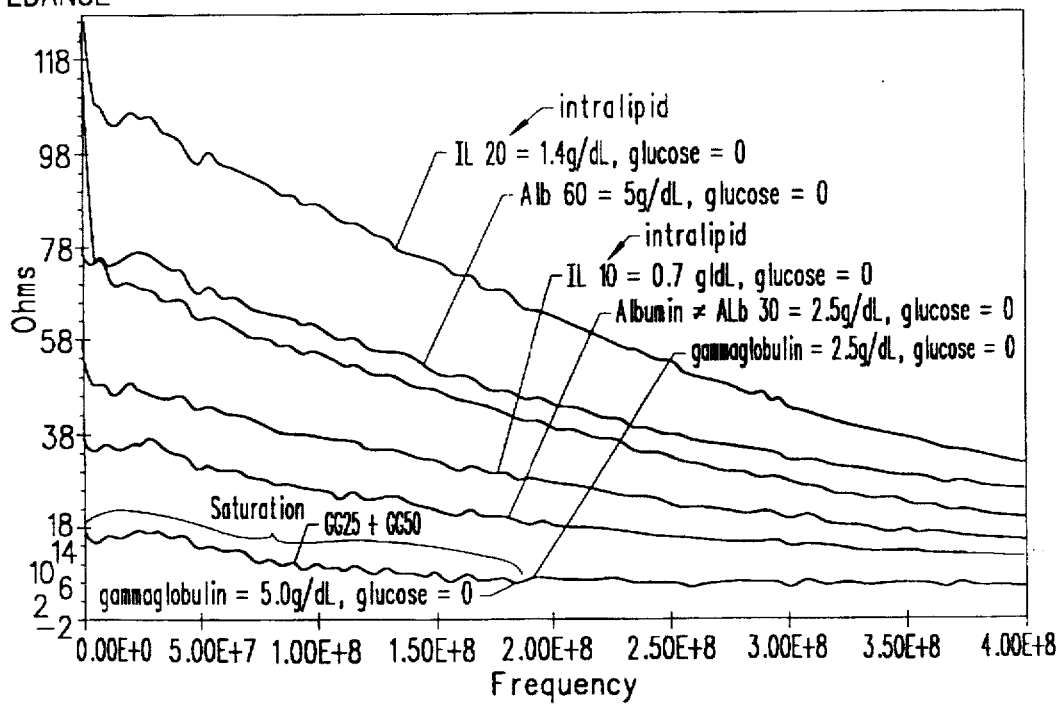
FIG. 8G depicts frequency versus impedance changes for a specimen containing various substances, and demonstrates a possible gamma globulin saturation region.

FIG. 8G depicts average impedance as a function of frequency ranging from about 1 MHz to about 0.4 GHz. Note that between about 0.1 and 0.2 GHz, gamma globulin appears to saturate.

In other experiments, applicants measured impedance magnitude using PBS at various temperatures to determine temperature sensitivity. These experiments disclosed that use of frequencies ranging from about 800 MHz to about 900 MHz provided impedance magnitude data that was temperature insensitive. The measurements were made using reflective mode, but the same result would apply to transmitted mode data. When using a non-invasive in-vivo measurement configuration such as shown in FIG. 5B, skin temperature at a subject's fingers can range from about 24° C. to about 37° C. In practice, it is recommended that in addition to other data, that data also be taken in the 800 MHz to 900 MHz temperature insensitive regime, to provide a measure of correction as needed for the other data.

To recapitulate, the present invention recognizes that electrolyte ion interference, especially NaCl, with glucose measurements can be reduced. In one application, the interference is effectively nulled out, using impedance magnitude measurements at a cross-over frequency. In another application, compensation for electrolyte ion effects upon glucose measurements are made. The configuration of FIG. 5A and likely that of FIG. 5B can predict total glucose concentration with acceptable specificity and error tolerance.

As noted, it is advantageous to make high frequency and low frequency measurements of various parameters to provide a good glucose concentration prediction (with good specificity) in a specimen. Preferably, low frequency regime data is taken over 21 or more frequencies, and high frequency regime data is taken over 81 or more frequencies. While the preferred embodiment used a network analyzer that provided discrete frequencies, one-at-a-time, the various frequencies could instead have been presented en masse, or as groups of frequencies, rather than as discrete separate frequencies.

High frequency, e.g., 1 GHz to perhaps 5 GHz, measurements of phase provide a good measure of electrolyte concentration, in which frequency regime the phase measurements are insensitive to glucose concentration. On the other hand, use of a 2.5 GHz cross-over frequency permits impedance magnitude indication of glucose concentrations, with little contribution from electrolyte concentrations. But the most sensitive measures of glucose concentration are obtained at lower frequencies, at which impedance magnitude is a measure of glucose concentration plus electrolyte concentration.

High frequency phase response was used to predict changes in NaCl concentration. This predicted NaCl concentration change was then used to predict the impedance magnitude change at low frequency due to electrolyte concentration change. The predicted low frequency electrolyte contribution was then subtracted from low frequency total impedance magnitude. The remainder was impedance change due to glucose concentration. In mathematical terms:

$$\Delta|NaCl|=CAL\_CURVE\_NaCl\_PHASE\_HI*\Delta Phase@high\ frequency\ \Delta Z_{NaCl}=CAL\_CURVE\_NaCl\_MAG\_LO*\Delta|NaCl|$$

$$\Delta Z_{glucose}=\Delta Z_{total}-\Delta Z_{NaCl}$$

$$\Delta|Glucose|=CAL\_CURVE\_GLU\_MAG\_LO*\Delta Z_{glucose}$$

The "CAL_CURVE" expression is derived from calibration equations. When calculating concentration changes from phase or impedance change, it is necessary to solve an appropriate calibration equation for an unknown, e.g., "x" in terms of a know, e.g., "y". NaCl calibration was made using a PBS baseline solution into which NaCl was added in 2 mM increments, up to 12 mM above normal PBS. A second NaCl calibration involved diluting a PBS solution with distilled water in 2 mM increments, to −12 mM from normal PBS, during which time the solution volume changed from about 588 μl to about 685 μl. However, the resultant calibration curve provided a linear response with an excellent fit, e.g., $R^2>0.999$. Glucose calibration involved three separate experiments using −10 mM PBS, normal PBS, and +10 mM PBS baseline solutions, into which glucose was added in 100 mg/dL increments to 500 mg/dL. The glucose response was quite linear with good correlation for the calibration curve.

In making experimental runs, error was defined as 100* (Predicted value−Actual value)/Actual value. On a run-to-run basis, NaCl concentration predictions were <3% and overall NaCl concentration predictions have <0.2% error. Overall, glucose concentration predictions had <13% error, and run-to-run glucose predictions had <23% error. These results are gratifying, although future embodiments will no doubt return even more accurate glucose predictions.

The prediction method has the advantage of being fairly sensitive to NaCl, whose low frequency response is stronger than that of glucose. Although NaCl changes may be predicted with accuracy using high frequency phase data, any error in such measurement tends to be "magnified" by the leveraging effect of NaCl at low frequencies relative to glucose. Ideally, compensation would occur at some frequency whereat the NaCl response and glucose response were closer in magnitude. Applicants are also examining use of mathematical derivatives of the impedance and phase data obtained with the present invention.

Modifications and variations may be made to the disclosed embodiments without departing from the subject and spirit of the invention as defined by the following claims.

What is claimed is:

1. A method, capable of in vivo operation, for determining concentration of glucose in the presence of a second substance that includes NaCl in a specimen that includes blood, the method including the following steps:

(a) subjecting said specimen to radio frequency signals having a frequency regime ranging from about 0.1 Mhz to about 5 Ghz;

(b) at a first frequency regime, using at least some of said radio frequency signals to obtain data proportional to magnitude of concentration of said second substance in said specimen;

(c) at a second frequency regime, using at least some of said radio frequency signals to obtain data proportional to combined concentration in said specimen of said glucose and said second substance; and (d) using data from said first frequency regime and data from said second frequency regime to obtain a measure of concentration of said glucose in said specimen.

2. The method of claim 1, wherein at step (a), at least some of said frequencies are presented sequentially.

3. The method of claim 1, wherein at step (a), at least some of said frequencies are presented simultaneously.

4. The method of claim 1, wherein at step (b), said first frequency regime ranges from about 1 GHz to about 3 GHz.

5. The method of claim 1, wherein at step (b), said data proportional to magnitude is obtained by measuring phase shift between radio frequency signals input to said specimen and radio frequency signals returned from said specimen.

6. The method of claim 1, wherein at step (c), said second frequency regime ranges from about 0.11 MHz to about 3 GHz.

7. The method of claim 1, wherein at step (c), said second frequency regime ranges from about 800 MHz to about 900 MHz, in which regime temperature effects upon data are minimized.

8. The method of claim 1, wherein at step (c), said data proportional to combined concentration is obtained by measuring magnitude of impedance at said specimen.

9. The method of claim 1, wherein at step (d) a concentration value determined in step (b) is subtracted from a combined concentration determined in step (c) to provide said measure of concentration of said glucose.

10. The method of claim 1, in which said method is carried out non-invasively on a human subject, and wherein step (a) includes coupling said radio frequency signals via at least one probe that contacts a distal portion of said subject's body.

11. A method, capable of in vivo operation, for determining concentration of glucose in the presence of a second substance that includes NaCl in a specimen that includes blood, the method including the following steps:

(a) subjecting said specimen to radio frequency signals at a cross-over frequency at which frequency concentration effects of said second substance are essentially nulled-out; and (b) determining from data taken at said cross-over frequency concentration of said glucose.

12. The method of claim 11, wherein said cross-over frequency is about 2.5 GHz.

13. The method of claim 11, wherein at step (b), said data is impedance data.

14. The method of claim 11, wherein step (a) is carried out non-invasively on a human subject by coupling said cross-over frequency via at least one probe that contacts a distal portion of said subject's body.

15. A system, capable of in vivo operation, for determining concentration of a first chemical in the presence of a second substance in a specimen, including:

a transmitter outputting radio frequency signals having a frequency regime ranging from about 0.1 MHz to about 5 GHz;

at least one probe, coupling to said transmitter, contacting a portion of said specimen; and a receiver-signal processor system, coupled to said at least one probe, that analyzes at least some of said radio frequency signals present at said probe;

said receiver-signal processor system providing data including at least impedance and/or phase shift present at an interface between said specimen and said at least one probe;

wherein data provided by said receiver-signal processor system is used to determine said concentration of said first chemical in said specimen.

16. The system of claim 15, wherein said transmitter transmits signals appropriate for a specimen that is human blood, for a said first chemical that is glucose, and for a said second chemical that includes NaCl, and wherein said transmitter includes a network analyzer.

17. The system of claim 15, wherein:

said specimen is a human subject including said subject's blood;

said first chemical is glucose;

said second chemical includes NaCl;

said transmitter transmits signals appropriate for discerning concentration of glucose present in NaCl within human blood; and said at least one probe contacts an exterior portion of a finger of said subject such that non-invasive data is provided by said system.

* * * * *

UNITED STATES PATENT AND TRADEMARK OFFICE
CERTIFICATE OF CORRECTION

PATENT NO. : 5,792,668
DATED : August 11, 1998
INVENTOR(S) : FULLER et al.

It is certified that error appears in the above-identified patent and that said Letters Patent is hereby corrected as shown below:

Column 7, line 34, reads "90 ms" but should read --30 ms--.

Signed and Sealed this

Sixteenth Day of February, 1999

Attest:

Attesting Officer

*Acting Commissioner of Patents and Trademarks*